United States Patent
Deckers et al.

(12) 
(10) Patent No.: US 6,372,234 B1
(45) Date of Patent: *Apr. 16, 2002

(54) PRODUCTS FOR TOPICAL APPLICATIONS COMPRISING OIL BODIES

(75) Inventors: Harm M. Deckers; Gijs van Rooijen; Joseph Boothe; Janis Goll; Maurice M. Moloney, all of Calgary (CA)

(73) Assignee: SemBioSys Genetics Inc., Calgary, Alberta (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/577,147

(22) Filed: May 24, 2000

Related U.S. Application Data

(63) Continuation-in-part of application No. 09/448,600, filed on Nov. 24, 1999, now Pat. No. 6,183,762, which is a continuation-in-part of application No. 09/084,777, filed on May 27, 1998, now Pat. No. 6,146,645.
(60) Provisional application No. 60/075,863, filed on Feb. 25, 1998, provisional application No. 60/075,864, filed on Feb. 25, 1998, provisional application No. 60/047,779, filed on May 28, 1997, and provisional application No. 60/047,753, filed on May 27, 1997.

(51) Int. Cl.$^7$ ............... A61K 7/00; A61K 9/127; B01F 3/08
(52) U.S. Cl. .............. 424/401; 424/400; 424/450; 514/937; 516/53
(58) Field of Search ............... 424/400, 401, 424/450; 514/937; 516/53

(56) References Cited

U.S. PATENT DOCUMENTS

| | | | |
|---|---|---|---|
| 3,971,856 A | | 7/1976 | Dattary |
| 4,025,658 A | | 5/1977 | Pominski et al. |
| 4,362,759 A | | 12/1982 | Harris |
| 5,602,183 A | | 2/1997 | Martin et al. |
| 5,643,583 A | | 7/1997 | Voultoury et al. |
| 5,683,710 A | | 11/1997 | Akemi et al. |
| 5,683,740 A | | 11/1997 | Voultoury et al. |
| 5,856,452 A | * | 1/1999 | Moloney et al. ............ 530/412 |

FOREIGN PATENT DOCUMENTS

| | | |
|---|---|---|
| WO | WO 96/21029 | 7/1996 |
| WO | WO 96/41543 | 12/1996 |
| WO | WO 98/27115 | 6/1998 |
| WO | WO 98/53698 | 12/1998 |

OTHER PUBLICATIONS

Aguilar et al., 1991, Journal of Texture studies 22(1):59–84.
Armentia et al., 1993., Clin. Exp. Allergy 23:410–415.
Cater et al., 1974, J. Am. Oil Chem. Soc. 51:137–141.
Cater et al., 1997, J. Am. Oil Chemists' Soc., 54:90A–93A.
Davies, P.L. et al. 1990, FASEB J. 4:2460–2468.
Holbrook et al., Plant Physiol., 1991, 97:1051–1058.
Huang 1992, Ann. Rev. Plant Mol. Biol. 43:177–200.
Jacks, T.J. et al., 1990, JAOCS, 67(6): 353–361.
Knauf, V.C., 1994, Fat. Sci. Techn. 96:408.
Kumar et al., 1995, INFORM 6 (11):1217–1240.
Lawhon et al., 1977, J. Am. Oil, Chem. Soc. 54:75–80.
Leber, R. et al., 1994, Yeast 10:1421–1428.
Millichip, M., et al., 1996, Biochemistry Journal, 31:333–337.
Monsalve et al., 1997, Clin. Exp. Allergy 27:833–841.
Murphy, D.J. and Cummins I., 1989, Phytochemistry, 28:2063–2069.
Murphy, D.J., 1993, INFORM, 4(8):922–932.
Ogawa et al. 1993, Biosci. Biotechnol. Biochem., 57(6):1030–1033.
Pieper–Fürst et al., 1994, J. Bacteriol. 176:4328–4337.
Ross et al., Plant Science, 1993, 93:203–210.
Roessler, P.G., 1988, J. Physiol. (London) 24:394–400.
Ting et al., 1997, Journal Biol. Chem. 272(6):3699–3706.

* cited by examiner

*Primary Examiner*—Jose' G. Dees
*Assistant Examiner*—Marina Lamm
(74) *Attorney, Agent, or Firm*—Bereskin & Parr; Micheline Gravelle

(57) ABSTRACT

The present invention provide novel emulsion formulations which comprise oil bodies. The invention also provides a method for preparing the emulsions and the use of the emulsions in products for topical application to the skin. The products are very mild to the skin and may be easily formulated into a wide variety of personal care and dermatological products.

10 Claims, 2 Drawing Sheets

PRODUCTS FOR TOPICAL APPLICATIONS COMPRISING OIL BODIES

This application is a continuation-in-part of U.S. patent application Ser. No 09/448,600 filed Nov. 24, 1999, now U.S. Pat. No. 6,183,762 which is a continuation-in-part of U.S. patent application Ser. No. 09/084,777 filed May 27, 1998 now U.S. Pat. No. 6,146,645 which claims benefit from U.S. provisional application Ser. No. 60/047,753, filed May 27, 1997; U.S. provisional application Ser. No. 60/047,779, filed on May 28, 1997; U.S. provisional application Ser. No. 60/075,863, filed on Feb. 25, 1998 and U.S. provisional application Ser. No. 60/075,864 filed on Feb. 25, 1998, all of which are incorporated herein by reference.

FIELD OF THE INVENTION

The present invention provides novel emulsions which comprise oil bodies. The invention also provides a method for preparing the emulsions and the use of the emulsions in various products that are topically applied to the surface area of the human body.

BACKGROUND OF THE INVENTION

Emulsions are mixtures prepared from two mutually insoluble components. It is possible to generate mixtures of homogenous macroscopic appearance from these components through proper selection and manipulation of mixing conditions. The most common type of emulsions are those in which an aqueous component and a lipophilic component are employed and which in the art are frequently referred to as oil-in-water and water-in-oil emulsions In oil-in-water emulsions the lipophilic phase is dispersed in the aqueous phase, while in water-in-oil emulsions the aqueous phase is dispersed in the lipophilic phase. Commonly known emulsion based formulations that are applied to the skin include cosmetic products such as creams, lotions, washes, cleansers, milks and the like as well as dermatological products comprising ingredients to treat skin conditions, diseases or abnormalities.

Generally emulsions are prepared in the presence of a multiplicity of other substances in order to achieve a desirable balance of emulsification, viscosity, stability and appearance. For example, the formulation of emulsions usually requires at least one, and frequently a combination of several, emulsifying agents. These agents facilitate the dispersal of one immiscible phase into the other and assist in stabilizing the emulsion. A comprehensive overview of emulsifying agents and their applications may be found in Becher, P. Encyclopedia of Emulsion Technology, Dekker Ed., 1983. Active agents beneficial to the skin, such as compounds to treat skin diseases, are also frequently formulated as emulsions in order to enhance their stability and to facilitate application of the active agent to the skin.

In the seeds of oilseed crops, which include economically important crops, such as soybean, rapeseed, sunflower and palm, the water insoluble oil fraction is stored in discrete subcellular structures variously known in the art as oil bodies, oleosomes, lipid bodies or spherosomes (Huang 1992, Ann. Rev. Plant Mol. Biol. 43: 177–200). Besides a mixture of oils (triacylglycerides), which chemically are defined as glycerol esters of fatty acids, oil bodies comprise phospholipids and a number of associated proteins, collectively termed oil body proteins. From a structural point of view, oil bodies are considered to be a triacylglyceride matrix encapsulated by a monolayer of phospholipids in which oil body proteins are embedded (Huang, 1992, Ann. Rev. Plant Mol. Biol. 43: 177–200). The seed oil present in the oil body fraction of plant species is a mixture of various triacylglycerides, of which the exact composition depends on the plant species from which the oil is derived. It has become possible through a combination of classical breeding and genetic engineering techniques, to manipulate the oil profile of seeds and expand on the naturally available repertoire of plant oil compositions. For an overview of the ongoing efforts in his area, see Designer Oil Crops/Breeding, Processing and Biotechnology, D. J. Murphy Ed., 1994, VCH Verlagsgesellschaft, Weinheim, Germany.

Plant seed oils are used in a variety of industrial applications, including the personal care industry. In order to obtain the plant oils used in these applications, seeds are crushed or pressed and subsequently refined using processes such as organic extraction, degumming, neutralization, bleaching and filtering. Aqueous extraction of plant oil seeds has also been documented (for example, Embong and Jelen, 1977, Can. Inst. Food Sci. Technol. J. 10: 239–243). Since the objective of the processes taught by the prior art is to obtain pure oil, oil bodies in the course of these production processes lose their structural integrity. Thus, the prior art emulsions formulated from plant oils generally do not comprise intact oil bodies.

Although fossil oil based products dominate certain markets, in other applications, oils derived from plant sources and fossil sources are in direct competition. Lauric oils, for example, which are widely used in the manufacture of detergents, are obtained from fossil oils as well as from coconut oil and more recently from genetically engineered rapeseed (Knauf, V. C., 1994, Pat. Sci. Techn. 96: 408). However, there is currently an increasing demand for biodegradable sources of raw materials. The plant oil body based emulsions of the present invention offer an advantage over similar mineral oil based formulations, in that the oil fraction is derived from a renewable and environmentally friendly source.

U.S. Pat No. 5,683,740 to Voultoury et al. and 5,613,583 to Voultoury et al. disclose emulsions comprising lipid vesicles that have been prepared from crushed oleagenous plant seeds. In the course of the crushing process, oil bodies substantially lose their structural integrity. Accordingly, these patents disclose that in the crushing process, 70% to 90% of the seed oil is released in the form of free oil. Thus the emulsions which are the subject matter of these patents are prepared from crushed seeds from which a substantial amount of free oil has been released while the structural integrity of the oil bodies is substantially lost. In addition, the emulsions disclosed in both of these patents are prepared from relatively crude seed extracts and comprise numerous endogenous seed components including glycosylated and non-glycosylated non-oil body seed proteins. It is a disadvantage of the emulsions to which these patents relate that they comprise contaminating seed components imparting a variety of undesirable properties, which may include allergenicity and undesirable odour, flavour, colour and organoleptic characteristics, to the emulsions. Due to the presence of seed contaminants, the emulsions disclosed in these patents have limited applications.

SUMMARY OF THE INVENTION

The present invention relates to novel emulsion formulations which are prepared from oil bodies. The emulsion formulations of the subject invention are obtainable in non-toxic and food grade forms. In addition, the emulsion formulations are advantageously prepared from an oil body preparation which is creamy in texture and thus may be readily applied in a variety of products that are topically applied to the skin. The present inventors have found that the oil body fraction of living cells is useful in the formulation of personal care and dermatological products. Broadly stated, the present invention provides an emulsion formulation for the application to the surface area of the human body comprising washed oil bodies derived from a cell.

The invention also provides methods for preparing the emulsion formulations and the use of the emulsion formulations for the application to the surface area of the human body.

Accordingly, the present invention provides a method for preparing emulsion formulations comprising: 1) obtaining oil bodies from a cell; 2) washing the oil bodies; and 3) formulating the washed oil bodies into an emulsion for application to the surface area of the human body.

In a preferred embodiment of the invention, the washed oil body preparation is obtained from plant seeds, including seeds obtainable from flax, safflower, rapeseed, soybean, maize and sunflower. Accordingly, the invention provides a method for preparing the emulsion formulations from plant seeds comprising:

(a) grinding plant seeds to obtain ground seeds comprising substantially intact oil bodies;
(b) removing solids from the ground seeds;
(c) separating the oil body phase from the aqueous phase;
(d) washing the oil body phase to yield a washed oil body preparation; and
(e) formulating the washed oil body preparation into an emulsion for application to the surface area of the human body.

In a preferred embodiment of the invention, a liquid phase is added to the seeds prior to or while grinding the seeds.

In a further preferred embodiment of the invention, formulating the emulsion comprises stabilizing the washed oil body preparation to prevent degradation of the oil bodies either by physical forces or chemical forces.

The emulsions of the present invention can be used in a wide range of applications including in the preparation of personal care and dermatological products. Additional advantages and features of the present invention will become apparent after consideration of the accompanying drawings and the following detailed description of the invention.

DETAILED DESCRIPTION OF THE INVENTION

Figure 1:
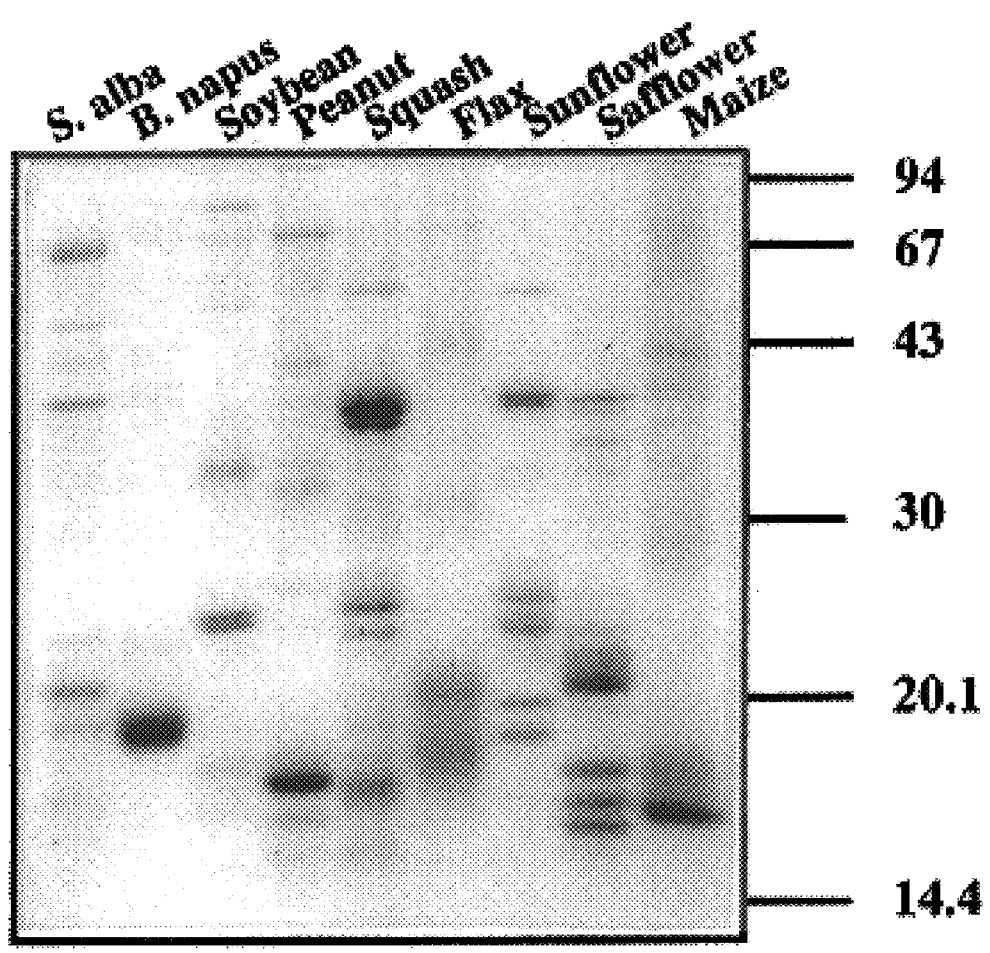
FIG. 1 is a Coomassie blue stained gel of a washed oil body preparation from white mustard, rapeseed (*Brassica napus*), soybean, peanut, squash, flax, sunflower, safflower and maize.

As hereinbefore mentioned, the present invention relates to emulsion formulations comprising oil bodies derived from a cell. In one embodiment, the present invention provides an emulsion formulation comprising washed oil bodies. In a preferred embodiment, the washed oil bodies comprise substantially intact oil bodies.

In another embodiment, the present invention provides a method for preparing an emulsion formulation comprising: 1) obtaining oil bodies from a cell; 2) washing the oil bodies; and 3) formulating the washed oil bodies into an emulsion for application to the surface area of the human body. Preferably, the washed oil bodies comprise substantially intact oil bodies.

In a preferred embodiment of the invention, formulating the washed oil bodies comprises stabilization of the washed oil bodies so that an oil body preparation is obtained that is chemically as well as physically stable.

The cell can be any cell that contains oil bodies (or oil body-like structures) including plant cells, animal cells, fungal cells and bacterial cells. In a preferred embodiment of the invention the oil bodies are obtained from a plant cell. The oil bodies may be obtained from a plant cell by rupturing the plant cell membrane and cell wall using any method which releases the cells constituents without substantially compromising the structural integrity of the oil bodies. More preferably, the oil bodies are obtained from plant seeds. Accordingly, the present invention further provides a method for preparing an emulsion formulation comprising:

(1) obtaining oil bodies from plant seeds by a method that comprises:
   (a) grinding plant seeds to obtain ground seeds comprising substantially intact oil bodies;
   (b) removing solids from the ground seeds; and
   (c) separating the oil body phase from the aqueous phase,
(2) washing the oil body phase to yield a washed oil body preparation; and
(3) formulating the washed oil body preparation into an emulsion for application to the surface area of the human body.

In a preferred embodiment of the invention, a liquid phase is added to the seeds prior to or while grinding the seeds.

The term "grinding" as used herein means milling, crushing, chopping or granulating the seeds and these terms may be used interchangeably throughout this application. Trn the process, the seed cells are broken open while the oil bodies remain substantially intact. The term "substantially intact" as used herein means that the oil bodies have not released greater than 50% (v/v) of their total seed oil content in the form of free oil. Preferably, grinding of the seeds results in release of less than about 50% (v/v) of the total seed oil content in the form of free oil, more preferably less than about 20% (v/v) and most preferably less than about 10% (v/v).

The term "solids" as used herein means any material that is not soluble in the aqueous phase or in the oil body phase, such as seed hulls.

The term "washing the oil bodies" as used herein means any process that removes cellular contaminants from the oil body phase, in particular any contaminant which imparts undesirable properties to the emulsion formulation, such as allergenic properties, undesirable color, odor, flavor or dermatological characteristics or any other undesirable property. Examples of methods of washing include gravitation based separation methods such as centrifugation and size exclusion based separation techniques such as membrane ultrafiltration and crossflow mnicrofiltration. Washing methods and conditions are selected in accordance with the desired purity of the oil body preparation.

The term "washed oil body preparation" as used herein means a preparation of oil bodies from which a significant amount of cellular material has been removed including contaminants which impart undesirable properties to the emulsion formulation, such as allergenic properties, undesirable color, odor, taste or organoleptic characteristics or any other undesirable property. Preferably, the washed oil body preparation contains less than about 75% (w/1w) of all endogenously present non-oil body seed proteins, more preferably the washed oil body preparation contains less than about 50% (w/w) of endogenously present non-oil body seed proteins and most preferably less than about 10%(w/w) of endogenously present non-oil body seed proteins.

By "formulating the oil bodies into an emulsion for application to the body", it is meant that the washed oil body preparation is mixed, homogenized or prepared until an emulsion is formed In a preferred embodiment, an additional ingredient is added, such as a liquid phase, and the washed oil body preparation and the additional ingredient are mixed until a homogenous mixture is attained.

The emulsion formulation of the present invention is prepared for topical application to the surface area of a human body in need thereof including without limitation for the improvement or benefit of the physical appearance, health, fitness or performance of the surface area of the human body.

The washed oil body preparations are particularly suitable for the formulation of emulsions for application to the surface area of the human body due to advantageous properties outlined below.

PROPERTIES OF THE OIL BODIES

The emulsion formulations of the present invention comprise substantially intact washed oil bodies of approximately uniform size, shape and density. When viewed under the electron microscope, oil bodies are found to be more or less spherically shaped structures (see: Example Murphy, D. J. and Cummins I., 1989, Phytochemistry, 28: 2063–2069; Jacks, T. J. et al., 1990, JAOCS, 67: 353–361). Typical sizes of oil bodies vary between 0.4 micrometer and 1.5 micrometer (Murphy, D. J. and Cummins 1., 1989, Phytochemistry, 28: 2063–2069). When analyzed using a Malvern Size Analyzer, it was found that oil bodies in a washed oil body preparation isolated from rapeseed were symmetrically and unimodally distributed around 1 micrometer. Using a Malvern Size Analyzer a washed oil body preparation could be clearly distinguished from commercially obtainable oil-in-water emulsions including soymilk, mayonnaise (Kraft Real Mayonnaise) and two coconut milk preparations (Tosca, Aroy-D). The exact size and density of the oil bodies depends at least in part on the precise protein/phospholipid/triacylglyceride composition which is present. Preparing washed oil bodies according to the present invention does not result in a substantive alteration in the shape of the oil bodies in comparison with those present in whole seed when viewed under the electron microscope.

Upon breaking open a cell containing oil bodies, the oil body fraction may be rapidly and simply separated from aqueous solutions since in aqueous solutions the oil body fraction will float upon application of centrifugal force. In solutions, where the density of the oil body fraction is greater than that of the solvent, such as 95% ethanol, the oil bodies will sediment under the same conditions. The oil body fraction may also be separated from the aqueous fraction through size-exclusion based separation techniques, such as membrane filtration, which may be advantageous in that more uniformly sized oil bodies may be acquired.

The oil bodies present in the washed oil body preparations of the present invention are resistant to exposure to strong acids and bases, including prolonged exposure to acidic conditions at least as low as pH 2 and alkaline conditions at least as high as pH 10. When exposed to pH 12, a slight loss of oil was observed, indicating a loss of integrity of the oil body structure. In addition, extraction with various organic solutions, including methanol, ethanol, hexane, isopropyl alcohol and ethyl acetate, does not or only slightly compromise the integrity of the oil bodies present in the washed oil body preparation. The oil bodies present in the washed oil body preparation were also found to withstand mixing with the anionic detergent, sodium dodecyl sulfate (SDS), the cationic, detergent hexadecyl trimethyl bromide and Tween-80, a non-ionic detergent. Boiling of the washed oil body preparation in the presence of SDS was found to result at least partly in disintegration of the oil body structure. The oil bodies present in the washed oil body preparation are stable when maintained for 2 hours up to at least 100° C. A slow freeze and thaw of washed oil body preparations resulted in a change in their physical appearance characterized by the formation of clumps as opposed to a homogeneous emulsion. Oil body clumping following a freeze-thaw could also be prevented to a large degree by either a) flash freezing in liquid nitrogen instead of slow freezing at −20° C. or b) adding glycerol in excess of 5% (v/v) to the oil body preparation prior to freezing. The resistance to relatively harsh chemical and physical conditions, is a unique characteristic of the oil bodies present in the washed oil body preparation of the subject invention.

The present invention provides emulsion formulations comprising oil bodies from which a significant amount of seed contaminants have been removed These contaminants include proteins, volatiles and other compounds which may impart undesirable color, odor, flavor, organoleptic characteristics or other undesirable characteristics, A number of seed proteins have been reported to cause allergenic reactions. For example, Ogawa et al. (1993, Biosci. Biotechnol. Biochem., 57:1030–1033) report allergenicity of the soybean glycoprotein P34 (alternatively referred to as Gly m Bd 30K). Allergenic reactions against rapeseed, wheat and barley seed proteins have also been reported (Armentia et al., 1993., Clin. Exp. Allergy 23: 410–415; Monsalve et al., 30 1993, Clin. Exp. Allergy 27: 833–841). Hience removal of contaminating seed proteins is advantageous. Washing conditions way be selected such that a substantially pure oil body preparation is obtained. In that case, only the oil body proteins are substantially present in the preparation.

For many applications, it is also considered desirable that a purer better defined oil body preparation is obtained, as this allows more control over the formulation process of the final emulsion In order for the washed oil body preparation to be included in a diverse set of emulsions it is desirable that volatiles are kept to a minimum and the color is preferably light or white. Washing of the oil body preparation results in a lighter colored preparation. In addition, a substantial amount of volatiles is removed. Also removed by washing are compounds which promote the growth of microorganisms as it was observed that a washed oil body preparation had a longer shelf life than an unwashed preparation. Other compounds which are removed by washing include anti-nutritional glucosinilates and/or breakdown products thereof and fibrous material. When heat treated to 60° C. or 80° C., it was observed that larger quantities of water remained absorbed by the washed oil body preparation when compared with an unwashed preparation. Upon cooling down to room temperature and centrifugation, it was observed that the washed oil body preparation remained stable, while phase separation occurred in the unwashed preparation. Given the enhanced stability of washed oil bodies, they are preferred where the formulation process involves the application of heat. When heated to 40° C., the washed oil body preparation was able to absorb a larger quantity of exogenously added water without resulting in phase separation. Thus in the formulation of aqueous emulsions, washed oil bodies are preferred. The capacity to absorb exogenously added oils was also compared between a preparation of washed oil bodies and an unwashed preparation. Larger amounts of exogenous oil could be added to the washed oil body preparation before an unstable emulsion was formed. This is advantageous in formulations where exogenous oils or waxes are added in the formulation process such as where personal care products are prepared. When viscosity was compared between a washed oil body preparation and an unwashed preparation it was found that the washed preparation was more viscous. A more viscous preparation of oil bodies is desirable as this allows for more flexibility in the formulation process and eliminates the need for the addition of thickening agents in the formulation process.

Thus the washed oil body preparation provided here is superior to an unwashed preparation in many respects. The washed oil body preparation of the present invention is a better defined preparation with a longer shelf life and more preferable color, odor and viscosity characteristics. The washed oil body preparation also has superior water and oil absorption characteristics. Finally due to the removal of a significant amount of seed proteins, allergenic reactions are less likely to occur. These characteristics allow the use of the washed oil body preparation in the formulation of a variety of domestic and industrial emulsions.

The above observations were made using washed and unwashed oil body preparations obtained from rapeseed and prepared as detailed in Example 2 of the present application. It is believed that resistance to relatively harsh chemical and physical conditions will be a characteristic of the oil bodies present in the washed oil preparation of the subject invention regardless of the source of the oil bodies. However one or more of the hereinbefore documented properties for rapeseed oil bodies may vary depending on the cells from which the washed oil bodies preparation is obtained. Nevertheless it is to be clearly understood that the subject invention is drawn to an oil body preparation which may be obtained from any cell comprising oil bodies.

In one embodiment of the present invention, the oil bodies are obtained from plant seeds. The presence of intact oil bodies in the emulsion and the described characteristics of these oil bodies clearly distinguish the subject emulsion formulation from other materials which may be prepared from plant seeds.

SOURCES AND PREPARATION OF THE OIL BODIES

The washed oil body preparation of the subject may be obtained from any cell containing oil bodies or oil body-like organelles. This includes animal cells, plant cells, fungal cells, yeast cells (Leber, R. et al., 1994, Yeast 10; 1421–1428), bacterial cells (Pieper-Furst et al., 1994, J. Bacteriol. 176: 4328–4337) and algae cells (Rossler, P. G., 1988, J. Physiol. (London) 24: 394–400).

In preferred embodiments of the invention the oil bodies are obtained from a plant cell which includes cells from pollens, spores, seed and vegetative plant organs in which oil bodies or oil body-like organelles are present (Huang, 1992, Ann. Rev. Plant Physiol. 43: 177–200).

More preferably, the washed oil body preparation of the subject invention is prepared from plant seeds. Among the plant seeds useful herein preferred are those seeds obtainable from plant species selected from the group of plant species consisting of almond (*Prunus dulcis*); anise (*Pimpinella anisum*); avocado (Persea spp.); beach nut (*Fagus sylvatica*); borage (also known as evening primrose) (*Boragio officinalis*); Brazil nut (*Bertholletia excelsa*); candle nut (*Aleuritis tiglium*); carapa (*Carapa guineensis*); cashew nut (*Ancardium occidentale*); castor (*Ricinus communis*); coconut (*Cocus nucifera*); coriander (*Coriandrum sativum*); cottonseed (Gossypium spp.); crambe (*Crambe abyssinica*); Crepis alpina; croton (*Croton tiglium*); Cuphea spp.; dill (*Anethum gravealis*); Euphorbia lagascae; Dimorphoteca pluvialis; false flax (*Camolina sativa*); fennel (*Foeniculum vulgaris*); groundnut (*Arachis hypogaea*); hazelnut (*coryllus avellana*); hemp (*Cannabis sativa*); honesty plant (*Lunnaria annua*); jojoba (*Simmiondsia chinensis*); kapok fruit (*Ceiba pentandra*); kukui nut (*Aleuritis moluccana*); Lesquerella spp., linseed/flax (*Linum usitatissimum*); macadamia nut (Macademia spp.); maize (*Zea mays*); meadow foam (*Limnanthes alba*); mustard (Brassica spp. and *Sinapis alba*); oil palm (*Elaeis guineeis*); oiticia (*Licania rigida*); paw paw (*Assimina triloba*); pecan (Juglandaceae spp.); perilla (*Perilla frutescens*); physic nut (*Gairopha curcas*); pilinut (*Canariuim ovatum*); pine nut (pine spp.); pistachio (*Pistachia vera*); pongam (*Bongamin glabra*); poppy seed (*Papaver soniferum*); rapeseed (Brassica spp.); safflower (*Carthamus tinctorius*); sesame seed (*Sesamum indicum*); soybean (*Glycine max*); squash (*Cucurbita maxima*); sal tree (*Shorea rubusha*); Stokes aster (*Stokesia laevis*); sunflower (*Helianthus annuus*); tukuma (Astocarya spp.); tung nut (*Aleuritis cordata*); vernolnia (*Verzonia galamensis*); and mixtures thereof.

More preferred for use herein are oil bodies obtained from plant seeds selected from the group of plant species consisting of Brazil (*Bertholletia excelsa*); castor (*Ricinus communis*); coconut (*Cocus nucifera*); coriander (*Coriandrum sativum,*); cottonseed (Gossypium spp.); groundnut (*Arachis hypogaea*); jojoba (*Simmmondsia chinensis*); linseed/flax (*Linum usitatissimum*); maize (*Zea mays*); mustard (Brassica spp. and Sinapis alba); oil palm (*Elaris guineeis*); olive (*Olea europaea*); rapeseed (Brassica spp.); safflower (*Cartharnus tinctorius*); soybean (*Glycine max*); squash (*Cucurbita maxima*); sunflower (*Helianthtus annuus*); and mixtures thereof.

Most preferred for use herein are oil bodies prepared from safflower (*Carthtamus tintctorius*).

Plants are grown and allowed to set seed using agricultural cultivation practises well known to a person skilled in the art. After harvesting the seed and if desired removal of material such as stones or seed hulls (dehulling), by for example sieving or rinsing, and optionally drying of the seed, the seeds are subsequently processed by mechanical pressing, grinding or crushing. In a preferred embodiment, a liquid phase is added prior to or while grinding the seeds. This is known as wet milling. Preferably the liquid is water although organic solvents such as ethanol may also be used. Wet milling in oil extraction processes has been reported for seeds from a variety of plant species including: mustard (Aguilar et a) 1990, Journal of Texture studies 22:59–84), soybean (U.S. Pat. No. 3,971,856; Carter et al., 1974, J. Am. Oil Chem. Soc. 51:137–141), peanut (U.S. Pat. No. 4,025, 658; U.S. Pat. No. 4,362,759), cottonseed (Lawhon et al., 1977, J. Am. Oil, Chem. Soc. 63.533–534) and coconut (Kumar et al., 1995, INFORM 6 (11):1217–1240). It may also be advantageous to imbibe the seeds for a time period from about fifteen minutes to about two days in a liquid phase prior grinding. Imbibing may soften the cell walls and facilitate the grinding process. Imbibition for longer time periods may mimic the germination process and result in certain advantageous alterations in the composition of the seed constituents. Preferably the added liquid phase is water.

The seeds are preferably ground using a colloid mill, such as the MZI30 (Fryma Inc.). Besides colloid mills, other milling and grinding equipment capable of processing industrial scale quantities of seed may also be employed in the here described invention including: flaking rolls, disk mills, colloid mills, pin mills, orbital mills, IKA mills and industrial scale homogenizers. The selection of the mill may depend on the seed throughput requirements as well as on the source of the seed which is employed. It is of importance that seed oil bodies remain substantially intact during the grinding process. Grinding of the seeds therefore results in the release of preferably less than about 50% (v/v) of the total seed oil content in the form of free oil, more preferably less than about 20% (v/v) and most preferably less than about 10% (w/w). Any operating conditions commonly employed in oil seed processing, which tend to disrupt oil bodies are unsuitable for use in the process of the subject invention. Milling temperatures are preferably between 10° C. and 90° C. and more preferably between 26° C. and 30° C., while the pH is preferably maintained between 2.0 and 10.

Solid contaminants, such as seed hulls, fibrous material, undissolved carbohydrates and proteins and other insoluble contaminants, are removed from the crushed seed fraction. Separation of solid contaminants, may be accomplished using a decantation centrifuge, such as a IIASCO 200 2-phase decantation centrifuge or a NX310B (Alpha Laval). Depending on the seed throughput requirements, the capacity of the decantation centrifuge may be varied by using other models of decantation centrifuges, such as 3-phase decanters. Operating conditions vary depending on the particular centrifuge which is employed and must be adjusted so that insoluble contaminating materials sediment and remain sedimented upon decantation. A partial separation of the oil body phase and liquid phase may be observed under these conditions.

Following the removal of insoluble contaminants, the oil body phase is separated from the aqueous phase. In a preferred embodiment of the invention a tubular bowl centrifuge is employed. In other embodiments, hydrocyclones, disc stack centrifuges, or settling of phases under natural gravitation or any other gravity based separation method may be employed. It is also possible to separate the oil body fraction from the aqueous phase employing size exclusion methods, such as membrane ultrafiltration and crossflow microfiltration. In preferred embodiments the tubular bowl centrifuge is a Sharples model AS-16 (Alpha Laval) or a AS46 Sharples (Alpha Laval). A critical parameter is the size of the ring dam used to operate the centrifuge. Ring dams are removable rings with a central circular opening varying, in the case of the AS-16, from 28 to 36 mm and regulate the separation of the aqueous phase from the oil body phase thus governing the purity of the oil body fraction which is obtained. In preferred embodiments, a ring dam size of 29 or 30 mm is employed when using the AS-16. The exact ring dam size employed depends on the type of oil seed which is used as well as on the desired final consistency of the oil body preparation. The efficiency of separation is further affected by the flow rate. Where the AS-16 is used flow rates are typically between 750–1000 ml/min (ring dam size 29) or between 400–600 ml/min (ring dam size 30) and temperatures are preferably maintained between 26° C. and 30° C. Depending on the model centrifuge used, flow rates and ring dam sizes must be adjusted so that an optimal separation of the oil body fraction from the aqueous phase is achieved. These adjustments will be readily apparent to a skilled artisan.

Separation of solids and separation of the aqueous phase from the oil body fraction may also be carried out concomitantly using a gravity based separation method such as 3-phase tubular bowl centrifuge or a decanter or a hydrocyclone or a size exclusion based separation method.

The compositions obtained at this stage in the process, generally are relatively crude and comprise numerous endogenous seed proteins, which includes glycosylated and non-glycosylated proteins and other contaminants such as starch or glucosinilates or breakdown products thereof. The present invention comprises the removal of a significant amount of seed contaminants. To accomplish removal of contaminating seed material, the oil body preparation obtained upon separation from the aqueous phase is washed at least once by resuspending the oil body fraction and centrifuging the resuspended fraction. This process yields what for the purpose of this application is referred to as a washed oil body preparation. The number of washes will generally depend on the desired purity of the oil body fraction. Depending on the washing conditions which are employed, an essentially pure oil body preparation may be obtained. In such a preparation the only proteins present would be oil body proteins. In order to wash the oil body fraction, tubular bowl centrifuges or other centrifuges such hydrocyclones or disc stack centrifuges may be used. Washing of oil bodies may be performed using water, buffer systems, for example, sodium chloride in concentrations between 0.01 M and at least 2 M, 0.1 M sodium carbonate at high pH (11–12), low salt buffer, such as 50 mM Tris-HC1 pH 7.5, organic solvents, detergents or any other liquid phase. In preferred embodiments the washes are performed at high pH (11–12). The liquid phase used for washing as well as the washing conditions, such as the plh and temperature, may be varied depending on the type of seed which is used. Washing at a number of different pH's between pH 2 and pH 11–12 may be beneficial as this will allow the step-wise removal of contaminants, in particular proteins. Preferably washing conditions are selected such that the washed oil body preparation comprises less than about 75% (w/w) of all endogenously present non-oil body seed proteins, more preferably less than about 50% (w/w) of endogenously present non-oil body seed proteins and most preferably less than about 10% (w/w) of endogenously present non-oil body proteins. Washing conditions are selected such that the washing step results in the removal of a significant amount of contaminants without compromising the structural integrity of the oil bodies. In embodiments where more than one washing step is carried out, washing conditions may vary for different washing steps. SDS gel electrophoresis or other analytical techniques may conveniently be used to monitor the removal of endogenous seed proteins and other contaminants upon washing of the oil bodies. It is not necessary to remove all of the aqueous phase between washing steps and the final washed oil body preparation may be suspended in water, a buffer system, for example, 50 mM Tris-HCl pH 7.5, or any other liquid phase and if so desired the pH may be adjusted to any pH between pH 2 and pH 10.

The process to manufacture the washed oil body preparation may be performed in batch operations or in a continuous flow process. Particularly when tubular bowl centrifuges are used, a system of pumps operating between steps (a) and (b), (b) and (c), and (c) and (d) a continuous flow throughout the processing system is generated. In a preferred embodiment, the pumps are 1 inch M2 Wilden air operated double diaphragm pumps. In other embodiments, pumps, such as hydraulic or peristaltic pumps may be employed. In order to maintain a supply of homogenous consistency to the decantation centrifuge and to the tubular bowl centrifuge, homogenizers, such as an IKA homogenizer may be added between the separation steps. In-line homogenizers may also be added in between various centrifuges or size exclusion based separation equipment employed to wash the oil body preparations. Ring dam sizes, buffer compositions, temperature and pH may differ in each washing step from the ring dam size employed in the first separation step.

In embodiments of the invention where the oil bodies are isolated from softer tissues, for example the mesocarp tissue of olives, the techniques applied to break open the cell may vary somewhat from those used to break harder seeds. For example, pressure-based techniques may be preferred over crushing techniques. The methodology to isolate oil bodies only a small scale has been reported for isolation of oil bodies from mesocarp tissues in olive (*Olea europaea*) and avocado (*Persea americana*) (Ross et al., Plant Science, 1993, 93: 203–230) and from microspore-derived embryos of rapeseed (*Brassica napus*) (Holbrook et al., Plant Physiol., 1991, 97: 1051–1058).

In embodiments of the invention where oil bodies are obtained from non-plant cells, the washed oil body preparation is isolated following similar procedures as outlined above. The methodology for isolating oil bodies from yeast has been documented (Ting et al., 1997, Journal Biol. Chem. 272.3699–3706).

The chemical and physical properties of the oil fraction may be varied in at least two ways. Firstly, different plant species contain oil bodies with different oil compositions. For example, coconut is rich in lauric oils ($C_{12}$), while erucic acid oils ($C_{22}$) are abundantly present in some Brassica spp. Secondly, the relative amounts of oils may be modified within a particular plant species by applying breeding and genetic engineering techniques known to the skilled artisan. Both of these techniques aim at altering the relative activities of enzymes controlling the metabolic pathways involved in oil synthesis. Through the application of these techniques, seeds with a sophisticated set of different oils are obtainable. For example, breeding efforts have resulted in the development of a rapeseed with a low erucic acid content (Canola) (Bestor, T. H., 1994, Dev. Genet. 15: 458) and plant lines with oils with alterations in the position and number of double bonds, variation in fatty acid chain length and the introduction of desirable functional groups have been generated through genetic engineering (Töpfer et al., 1995, Science, 268: 681–685). Using similar approaches a person skilled in the art will be able to further expand on the presently available sources of oil bodies. Variant oil compositions will result in variant physical and chemical properties of the oil bodies. Thus by selecting oilseeds or mixtures thereof from different species or plant lines as a source for oil bodies, or by mixing oil bodies obtained from various species or plant lines, a broad repertoire of emulsions with different textures, different properties that are beneficial to the skin and different viscosities may be acquired.

FORMULATING THE EMULSION

The washed oil body preparation may be formulated into an emulsion using techniques known in the art. Preferably, at least one additional ingredient is added to the washed oil body preparation. The additional ingredient may be any chemical compound, including without limitation any acid or base, any organic or inorganic molecule, any ionic or non-ionic compound, any polar or non-polar molecule and any lipophilic or hydrophilic compound or, if more than one additional ingredient is added, any mixture of these compounds. The additional ingredient may be added in any desirable form, for example, the additional ingredient may be added as a solution, suspension, a gel, a crystal, a liquid or solid and the additional ingredient may be of any desirable viscosity. Quantities of the additional ingredient may be as desired and will depend on the formulation. The additional ingredient may upon formulation become associated with the oil bodies for example by the formation of non-covalent or covalent chemical bonds with the oil body, remain suspended in solution, or form a suspension in which the oil bodies are dispersed. The additional ingredient may also penetrate the phospholipid monolayer surrounding the oil body or the triacylglyceride matrix. In a further preferred embodiment the liquid phase is water. Water may be added either directly or through moisture associated with another ingredient. The final amount of water is not critical, however generally, the compositions will contain at least 1% of water and up to 99% water.

The concentration of oil bodies in the final product may be as desired. Typically the final concentration of oil bodies varies from about 0.0000001% (w/v) to about 99.9999999% (w/v). Preferably the final concentration of oil bodies will vary from about 1% (w/v) to about 99% (w/v) and more preferably from about 2% (w/v) to about 60% (w/v). The final formulation may be a liquid or a solid and of any viscosity but in general the final formulation will be of a consistency and viscosity compatible with its use as a topically applied product.

In the course of the formulation process the oil bodies generally will stay intact, however depending on the ingredients that are added or the formulation process employed, the oil body structure may be more or less disrupted and the oil bodies may completely or partially disintegrate.

In the course of the formulation process any type of emulsion may be formed, including without limitation an oil-in-water emulsion, a water-in-oil emulsion, a multiple (e.g. double, tri-multiple, quarter-multiple and quinque-multiple etch) emulsion, and reverse emulsion. The compositions of the present invention preferably will be in the form two phases where one phase is uniformly dispersed in the other phase, and resulting in a homogenous macroscopic appearance. Where compositions comprising two or more non-uniformly dispersed phases are formed they generally need to be shaken or stirred prior to application of the emulsion to the surface area of the body.

The final formulation may be of any pH, but Is preferably of a pH compatible with application of the emulsion to the human skin. Usually the formulation process will require mixing to provide an adequate emulsion and it may be necessary to apply heat, pressure, freezing, one or more cycles of freeze thawing or other physical forces to formulate the emulsion.

The emulsion formulations for application to the surface area of the human body may comprise a wide variety of additional components and may be formulated in a wide range of products including personal care and dermatological products. The following optional ingredients and mixtures thereof represent non-limiting examples of ingredients that may be formulated with oil bodies in order to prepare a composition for topical application to the surface area of the human body.

Emulsion Stabilizing Agents

In a preferred embodiment of the present invention, the washed oil body preparation is stabilized so that an emulsion is obtained which may be stored for longer periods of time. For the purpose of the present application the term "stabilized oil body preparation" refers to an oil body emulsion that is prepared so that the oil body emulsion does not undergo undesirable physical or chemical alterations when the oil body emulsion is stored for long periods of time. Preferably the oil body preparation is prepared to be stable for at least 1 month, more preferably the preparation is stable for at least 1 year, and most preferably the preparation is stable at least 2 years when stored at room temperature. In a further preferred embodiment, the oil body emulsion is prepared so that the preparation additionally can withstand temperature fluctuations such as those which typically occur in non-temperature controlled environments for example during transport. In a stable oil body preparation alterations over time with respect to color, odor, viscosity, texture, pH and microbial growth are minimal or absent.

Generally, the emulsion formulations will be treated such that contamination by bacteria, fungi, mycoplasmas, viruses and the like or undesired chemical reactions, such as oxidative reactions are prevented. In preferred embodiments this is accomplished by the addition of preservatives, for example sodium metabisulfite; Glydant Plus; Phenonip; methylparaben; propylparaben; Germall 115; Germaben II; phytic acid; and mixtures thereof. The preparation may also be stabilized by irradiation, for example by ionizing radiation such as cobalt-60 or cesium-137 irradiation or by ultraviolet irradiation or by heat treatment for example by pasteurization in a constant temperature water bath at approximately 65° C. for 20 minutes. The pasteurization temperature preferably ranges between 50° C. and 90° C. and the time for pasteurization preferably ranges between 15 seconds to 35 minutes.

Oxidative reactions may be prevented by the addition of anti-oxidants such as for example butylated hydroxytoluene (BHT); butylated hydroxyaniscol (BHA); ascorbic acid (vitamin C); tocopherol; phytic acid; citric acid; pro-vitamin A; and mixtures thereof.

The physical stability of the formulation may be further enhanced by the addition of for example an emulsifier such as an Arlacel such as Arlacel 165 or Glucamate LT or by the addition of viscosity modifiers such as such as cetyl alcohol; glycerol or Keltrol. The emulsion may be thickened and stabilized using gelling agents such as cellulose and derivatives; Carbopol and derivatives; carob; carregeenans and derivatives; xanthane gum; sclerane gum; long chain alkanolamides; bentone and derivatives; Kaolin USP; Veegum Ultra; Green Clay; Bentonite NFBC; and mixtures thereof. These agents are typically present in concentrations less than about 2% by weight.

The oil body preparation may also be further stabilized by modifying the pH and by modifying the ionic strength for example by adjusting the concentration of calcium or sodium ions. Examples of formulations of stabilized oil body preparations are shown in Example 6.

The following additional ingredients may be formulated with the stabilized oil body formulation. While in preferred embodiments of the present invention, the oil bodies are stabilized prior to the formulation with these additional ingredients, it is nevertheless possible to formulate the oil body preparation and stabilize the final formulation.

Surfactants

The emulsions of the present invention may comprise surfactants (i.e. a surface active agent) generally in a concentration varying from about 0.01% (w/v) to about 40% (w/v), and more preferably from about 0.05% (w/v) to about 15% (w/v) and most preferably from about 0.1% (w/v) to about 10% (w/v) selected from the group consisting of anionics, cationic,s, nonionics and amphoterics or mixtures thereof. The surfactants used herein may act in a variety of ways including without limitation as a cleansing agent, detergent, emulsifier, wetting agent, foam booster, foam depressent, conditioner or germicide. A wide variety of surfactants may be used in the formulation of the products herein disclosed. They include the surfactants disclosed in U.S. Pat. No. 5,151,209 to McCall et al.,; U.S. Pat. No. 5,151,210 to Steuri et al.; U.S. Pat. No. 5,120,532 to Wells et al.; and U.S. Pat. No. 5,635,469 to Fowler et al. all of which are incorporated herein by reference in their entirety Anionic surfactants that may be used in the formulation of the emulsions of the present invention include without limitation branched and unbranched alkyl and acyl hydrocarbon compounds, sodium dodecyl sulfate (SDS); sodium lauryl sulfate (SLS); sodium lauryl ether sulfate (SLES); sarconisate; fatty alcohol sulfates, including sodium, potassium, ammonium or triethaniolamine salts of $C_{10}$ to $C_{18}$ saturated or unsaturated forms thereof; ethoxylated fatty alcohol sulfates, including alkyl ether sulfates; alkyl glyceryl ether sulfonate, alpha sulpho fatty acids and esters; fatty acid esters of isethionic acid, including Igepon A; acyl (fatty) N-methyltaurides, including Igepon T; dialkylsulfo succinate esters, including $C_8$, $C_{10}$ and $C_{12}$ forms thereof; Miranot BT also referred to as lauroamphocarboxyglycinate and sodium tridecath sulfate; N-acylated amino acids, such as sodium N-lauroyl sarconisate or gluconate; sodium coconut monoglyceride sulfonate; and fatty acid soaps, including sodium, potassium, DEA or TEA soaps.

Among the cationic surfactants that are useful are monoalkyl trimethyl quartenary salts; dialkyl dimethyl quartenary salts; ethoxylated or propoxylated alkyl quaternary amonium salts, also referred to in the art as ethoquats and propoquats; cetyl benzylmethylalkyl ammonium chloride; quaternized imidazolines, which are generally prepared by reacting a fat or fatty acid with diethylenetriamine followed by quaternization, and non-fat derived cationic polymers such as the cellulosic polymer, Polymer JR (Union Carbide).

Further useful cationic surfactants include lauryl trimethyl ammonium chloride; cetyl pyridinium chloride; and alkyltrimethylammonium bromide. Cationic surfactants are preferably used in the formulation of hair care products and more preferably in the formulation of rinses and conditioners.

Useful nonionic surfactants include polyethoxylated compounds and polypropoxylated products. Polyethoxylated and polypropoxylated compounds may be prepared by reacting fatty alcohols with ethylene oxide or glycol or by reacting fatty alcohols with propylene oxide or glycol. These materials have the general formula $R(X)_nOR'$ wherein R is H or $C_{10}$ to $C_{30}$ alkyl group, X is —$OCH_2CH_2$— (i.e. when derived from ethylene oxide or glycol) or —$OCH_2CHCH_3$— (i.e. when derived from propylene oxide or glycol), n is an integer from about 1 to 100, and R' is 1–1 or a $C_{10}$ to $C_{30}$ alkyl group. Polyethoxylated and polypropoxylated products may also be prepared by reacting fatty acids with ethylene oxide or glycol or propylene oxide or glycol respectively. These materials have the general formula $RCO(X)_nOH$, wherein R is H or a $C_{10}$ to $C_{30}$ alkyl group, X is —$OCH_2CH_2$— (i.e. when derived from ethylene oxide or glycol) or —$OCH_2CHCH_3$— (i.e. when derived from propylene oxide or glycol) and n is an integer from about 1 to 100. Still other nonionic surfactants are the condensation products of a mixture of fatty acids and fatty alcohols reacting with ethylene glycol or oxide or propylene glycol or oxide. These materials have the general formula RCO(X)nR' wherein R and R' are 11 or $C_{10}$ to $C_{30}$ alkyl groups, X is —OCH$_2$CH$_2$— (i.e. when derived from ethylene oxide or glycol) or —OCH$_2$CHCH$_3$— (i.e. when derived from propylene oxide or glycol), and n is an integer from about 1 to 100.

Examples of ethoxylated and propoxylated non-ionic surfactants include ethoxylated anhydrohexitol fatty esters, for example Tween 20; mono- and diethanolamides; Steareth-20, also known as Volpo20; polyethylene glycol fatty esters (PEGs), such as PEG-8-stearate, PEG-8 distearate; block co-polymers, which are essentially combinations of hydrophylic polyethoxy chains and lipophilic polypropoxy chains and generically known as Poloaxamers.

Still other useful non-ionic surfactants include fatty esters of polyglycols or polyhydric alcohols, such as mono and diglyceride esters; mono- and di- ethylene glycol esters; diethylene glycol esters; sorbitol esters also referred to as Spans; sucrose esters; glucose esters; sorbitan monooleate, also referred to as Span80; glyceryl monostearate; and sorbitan monolaurate, Span20 or Arlacel 20.

Yet other useful nonionic surfactants include polyethylene oxide condensates of alkyl phenols and polyhydroxy fatty acid amide surfactants which may be prepared as for example disclosed in U.S. Pat. No. 2,965,576 to E. R. Wilson.

Examples of amiphoteric surfactants which can be used in the compositions of the present invention include the betaines, which can be prepared by reacting an alkyldimethyl tertiary amine, for example lauryl dimethylanmine with chloroacetic acid. Betaines and betaine derivatives include higher alkyl betaine derivatives including coco dimethyl carboxymethyl betaine; sulfopropyl betaine; alkyl amido betaines; and cocoamido propyl betaine. Sulfosultaines which may be used include for example, cocoamidopropyl hydroxy sultaine. Still other amphoteric surfactants include imidazoline derivatives and include the products sold under the trade name "Miranol" described in U.S. Pat. No. 2,528,378 which is incorporated herein by reference in its entirety. Still other amphoterics include phosphates for example, cocoamidopropyl PG-dimonium chloride phosphate and alkyldimethyl amine oxides.

Moisturizers

Another ingredient which may be formulated with the washed oil body emulsions of the present invention is a moisturizer. As used herein a "moisturizer" is an ingredient which promotes the retention of water to the surface area of the human body, including hair and skin. The term moisturizer as used herein includes both components which deliver water to the skin, also commonly referred to in the art as "humectant", and components which prevent the loss of water from the skin, also commonly referred to in the art as "occlusive". The moisturizer will generally comprise from about 0.1% (w/v) to about 99% (w/v), more preferably from about 0.5% (w/v) to about 50% (w/v), and most preferably from about 1% (w/v) to about 40% (w/v) of the final composition. Although the ingredients mentioned herein are generally defined as moisturizers they may also possess other properties such as emolliency or other conditioning properties.

Moisturizers that may used in accordance with the present invention include without limitation polyhydroxy alcohols, including butylene glycol, hexylene glycol, propylene glycol, sorbitol and the like; lactic acid and lactate salts, such as sodium or ammonium salts; $C_3$ and $C_6$ diols and triols including hexylene glycol, 1,4 dihydroxyhexane, 1,2,6-hexane triol; aloe vera in any of its forms, for example aloe vera gel; sugars and starches; sugar and starch derivatives, for example alkoxylated glucose; hyaluronic acid; lactamide monoethanolamine; acetamide monoethanolainine; glycolic acid; alpha and beta hydroxy acids (e.g. lactic, glycolic salicylic acid); glycerine; pantheol; urea; vaseline; natural oils; oils and waxes (see: the emollients section herein) and mixtures thereof. Moisturizers are generally recognized in the art of personal care and skin care and in principle any moisturizer may be formulated in the presence of oil bodies.

Emollients

A further ingredient which may be formulated with the oil body compositions of the present invention is an emollient. Emollients typically comprise between from about 0.01% to about 25%, preferably from about 0.05% to about 15% and more preferably from about 0.1% to about 10% w/v of the total formulation. Emollients are used to add or replace lipids and natural oils to the surface area of the human body. The term emollient as used herein is intended to include conventional lipids (for example, oils, waxes, lipids and other water insoluble components) and polar lipids (lipids which have been modified in order to increase water solubility typically through esterfication of a lipid to a hydrophylic moiety for example hydroxy groups, carbonyl groups and the like). Emollients which may be used in the present invention are preferably selected from the group consisting of natural oils and preferably plant-derived and essential oils, esters, silicone oils, polyunsaturated fatty acids (PUFAs), lanoline and its derivatives and petrochemicals.

Natural oils which may be used in accordance with the present invention may be obtained from sesame; soybean; apricot kernel; palm; peanut; safflower; coconut; olive; cocoa butter; palm kernel; shea butter; sunflower; almond; avocado; borage; carnauba; hazel nut; castor; cotton seed; evening primrose; orange roughy; rapeseed; rice bran; walnut; wheat germ; peach kernel; babassu; mango seed; black current seed; jojoba; macadeinia nut; sea buckthorn; sasquala; isubaki; mallow; meadowfoam seed; coffee; emu; mink; grape seed; thistle; tea tree; pumpkin seed; kukui nut; and mixtures thereof.

Esters which may be used include $C_8$–$C_{30}$ alklyl esters of $C_8$–$C_{30}$ carboxylic acids; $C_1$–$C_6$ diol monoesters and diesters of $C_8$–$C_{30}$ carboxylic acids; $C_{10}$–$C_{20}$ alcohol monosorbitan esters, $C_{10}$–$C_{20}$ alcohol sorbitan di- and tri-esters; $C_{10}$–$C_{20}$ alcohol sucrose mono-, di-, and tri-esters and $C_{10}$–$C_{20}$ fatty alcohol esters of $C_2$–$C_6$ 2- hydroxy acids and mixtures thereof. Examples of these materials include isopropyl palmitate; isopropyl myristate; Isopropyl isononate; $C_{12}/C_{14}$ benzoate ester (also known as Finesolve); sorbitan palmitate, sorbitan oleate; sucrose palmitate; sucrose oleate; isostearyl lactate; sorbitan laurate; lauryl pyrrolidone carboxylic acid; panthenyl triacetate; and mixtures thereof.

Further useful emollients include silicone oils, including non-volatile and volatile silicones. Examples of silicone oils that may be used in the compositions of the present invention are dimethicone; cyclomethycone; dimethycone-copolyol; aminofunctional sili cones; phenyl modified silicones; alklyl modified silicones; dimethyl and diethyl polysiloxane; mixed $C_1$–$C_{30}$ alkyl polysiloxane; and mixtures thereof. Additionally useful silicones are described in U.S. Pat. No. 5,011,681 to Ciotti et al., incorporated by reference herein.

A yet further useful group of emollients which may be formulated in accordance with the present invention in the presence of oil bodies are Janoline and lanoline derivatives for example lanoline esters.

Petrochemicals which may be used as emollients in the compositions of the present invention include mineral oil; petrolatum; isohexdecane; permethyl 101; isododecanol; $C_{11}$–$C_{12}$ Isoparrafin, also known as Isopar H.

Among the waxes which may be included in the compositions of the present invention are animal waxes such as beeswax; plant waxes such as carnauba wax, candelilla wax, ouricurry wax, Japan wax or waxes from cork fibres or sugar cane. Mineral waxes, for example paraffin wax, lignite wax, microcrystalline waxes or ozokerites and synthetic waxes may also be included.

It is noted that although the ingredients mentioned herein are generally defined as emollients they may also possess other properties such as moisturization or other conditioning properties (see under: Moisturizers, hereinbefore mentioned).

Fragrances

A further ingredient that may be formulated with the washed oil body compositions in accordance with the present invention is a fragrance. Typically a fragrance comprises between about 0.0001% (v/v) and about 25%) (v/v) of the final composition, more preferably between about 0.001% (v/v) and 10% (v/v) and most preferably between 0.01% (v/v) and 5% (v/v) of the final composition. For the purpose of the present application the term "fragrance" is meant to encompass any component reacting with the human olfactory sites and imparting a pleasurable odor, essence or scent. Fragrances that may be used in accordance with the present invention include any synthetic as well as natural fragrance and mixtures thereof. Typically a multiplicity of fragrances are used to achieve the desired effect. Those of skill in the art further recognize the terms "top note" (i.e. fragrances having a high vapor pressure), "middle note" (i.e. fragrance having a medium vapor pressure) and "base note" (i.e. fragrances having a low vapor pressure). Recognizing that categorization within these classes may depend to some extent on the fragrance formulator, the emulsions of the present invention may comprise any top note, middle note and base note fragrance. A further way of classifying fragrances is in accordance with generally recognized scents they produce. Descriptors used by those skilled in the art of fragrances are inter alia "rose", "floral", "green", "citrus", "spicy", "honey", "musk", "herbal", "jasmin", "lilac", lily of the valley", "orange", "peach", "oriental", "watermelon" "chypre" and "lemon", "woody", "fruity" all of which fragrances thus classified may be formulated with the emulsions of the present invention.

Fragrances that may be used in accordance with the present invention include linear and cyclic alkenes (i.e. terpenes); primary, secondary and tertiary alcohols; ethers; esters; ketones; nitrites; and saturated and unsaturated aldehydes; or mixtures thereof.

Examples of synthetic fragrances that may be used in accordance with the present invention include without limitation acetanisole; acetophenone; acetyl cedrene; methyl nonyl acetaldehyde; musk anbrette; heliotropin; citronellol; sandella; methoxycitranellal; hydroxycitranella); phenyl ethyl acetate; phenyletlhylisobutarate; gamma methyl ionone; geraniol; anetlhole; benzaldehyde; benzyl acetate; benzyl salicate; linalool; ciitiamic alcohol; phenyl acetaldehyde; amyl cinnamic aldehyde; caphore; p-tertiairy butyl cyclohexyl acetate; citral; cinnamyl acetate; citral diethyl acetal; coumarin; ethylene brasslate.; eugenol; 1-mentlhol; vanillin; and mixtures thereof.

Examples of natural fragrances of use herein include without limitation lavandin; heliotropin; sandlewood oil; oak moss; pathouly; ambergris tincture; ambrette seed absolute; angelic root oil; bergamont oil; benzoin Siam resin; buchu leaf oil; cassia oil; cedarwood oil; cassia oil; castorcum; civet absolute; chamomile oil; geranium oil; lemon oil; lavender oil; Ylang Ylang oil; and mixlures thereof.

A list of generally used fragrance materials can be found in various reference sources, for example, "Perfume and Flavor Chemicals", Vols. 1 and II; Steffen Arctander Allured Pub. Co. (1994) and "Perfumes: Art, Science and Technology"; Muller, P. M. and Lamparsky, D., Blackie Academic and Professional (1994) both incorporated herein by reference.

Active Ingredients

In accordance with the present invention a wide variety of active ingredients may be formulated with the washed oil bodies of the present invention. The terms "actives", "active agent" and "active ingredient" as used herein refers to a compound capable of enhancing or improving the physical appearance, health, fitness or performance of the surface area of the human body, including the skin, hair, scalp, teeth and nails. The amount of active formulated will depend on the desired effect and the active that is selected. In general, the amount of active varies from about 0.0001% (w/ v) to about 50% (w/v). More preferably however the amount of active in the final composition will vary from about 0.01% (w/v) to about 20% (w/v) and most preferably from about 0.1% (w/v) to about 10%/ (w/v). The actives may be formulated into the washed oil body formulation in any desired manner (e.g. mixed, stirred) under any desired condition (e.g. heated; under pressure) and in any desired form (e.g. a liquid, solid, gel, crystal, suspension). Depending on the chemical nature of the active and the formulation methodology, the active may become incorporated in the final formulation in a variety of ways, for example the active ingredient may remain suspended in solution, or form a suspension in which the oil bodies are dispersed, or the active ingredients may penetrate the phospholipid mono layer surrounding the oil body or the triacyl glyceride matrix of the oil body. The active also may be associated with the oil bodies. As used herein the term "associated with the oil bodies" refers to any specific interaction between the active ingredient and the oil bodies including any interaction which involves the formation of a covalent bond between the oil body and the active ingredient as well as any interaction which involves the formation of a non-covalent bond, for example an ionic bond, between the oil body and the active ingredient. The active agent may directly associate with the oil body or indirectly via one or more intermediate molecules. As used herein "crosslinker" or "crosslinking agent" means any single molecule or plurality of inter-linked molecules capable of indirectly associating the active ingredient with the oil body. Oil bodies crosslinked to actives may comprise a plurality of covalent and non-covalent interactions or mixtures thereof. Generally the reaction to crosslink the active ingredient to the oil body will involve the oleosin protein or oil body phospholipids as reactive groups.

Particularly useful crosslinking agents in this regard are those crosslinking agents which arc capable of reacting with oleosin proteins. These include homobifunctional crosslinkers (i.e. having two identical reactive groups) including homobifunctional imido esters and homobifunctional N-hydroxysuccinimidyl (NHS) esters; and heterobifunctional crosslinkers (i.e. having two different reactive groups), including crosslinkers comprising an amine reactive group; sulfhydryl reactive N-hydroxysuccinirnidyl esters such as maleimides pyridyl disulfides and alpha-haloacetyls; or a carboxyl reactive group. Non-limiting examples of crosslinking agents are inter alia dimethyladipimidate, discuccinidyl glutarate; succinimidyl 4-(N-maleimidomethyl) cyclo hexane-1-carboxylate, bis-maleimidohexane;sulfosuccinimidyl (4-iodoacetyl)-aminobenzoate; N-succinimidyl 3-(2-pyridyldithione)-propionate; and 1-etlyl-3(3-diinethylaminopropyl)-carbodiimide; glutaraldehyde.; and glyoxal.

Other useful crosslinkers include photoreactive crosslinkers such as arylazide derived compounds, for example p-azidophenyl glyoxal monohydrate; n-hydrosulfo-succinimidyl 4-azidobenzoate; and sulfosticcinimidyl (4-azidophenyldithio) propionate.

Still other components that are particularly useful as crosslinkers for the association of active ingredients to oil bodies are biotin-streptavidin and biotin-avidin crosslinkers (available from Pierce). By linking the active ingredient to streptavidin or avidin and biotinylating the oil bodies, or visa versa, biotinylating the active ingredient and linking avidin or streptavidin to the oil bodies, the active ingredient is crosslinked to the oil bodies via two inter-linked molecules. Still further useful cross-linking compounds which may be used in accordance with the present invention are one or more inter-linking antibodies. Particularly useful in this regard are antibodies with an affinity to oleosins. Combined inter-linked antibody-avidil-biotin or antibody-streptavidin-biotin cross-linkers may also be used in accordance with the present invention. Additional cross-linking strategies for associating compounds to oil bodies are described in PCT Patent Application WO 98/27115 to Moloney et al. which is incorporated by reference herein.

Non-limiting examples of actives which may be formulated in the presence of oil body emulsions are listed below. The actives are categorized in various classes however this classification is not intended to limit the actives in any way to only to those actives belonging to the categories herein mentioned.

(a) Sunscreen Actives

A wide variety of sunscreen actives are useful herein. The exact amount and type of sunscreen that is used depends on the level of photoprotection that is desired. Generally any agent offering protection against ultraviolet radiation by absorbing, scattering or reflecting the ultraviolet radiation may be used herein. The sunscreen agents used herein may offer protection against one or more of the following forms of sunlight radiation UVA, UVB, IJVC, visible light and infrared radiation. Generally the sunprotection factor (SPF) in the final formulation varies between 2 and 30, although products with SPFs up to 100 may be formulated. The sunscreen used herein may offer chemical or physical photoprotection.

Sunscreens which may be used in accordance with the present invention include those selected from the group comprising amino benzoic acid and derivatives, such as para-amino benzoic acid (PABA), glyceryl-PABA (Lisadimate), Padimate O, Roxadimate; anthrinalates, including methylanthrynilate; benzophenones, including dioxybenzone, oxybenzone and sulisobenzone, 3-benzophenone (Uvinul M40) 4-N,N-dimethylaminobenzoic acid ester with 2,4-dihydroxybenzophenone; camphor derivatives including 3-(4-methylbenzylidene) camphor, 3-benzylidene camphor; cinnamates including DFA-p-methoxycinnamate, ethylhexyl p-methoxy cinnamate, octocrylene, octyl methoxy cinnamate (Parasol MCX); dibenzoyl methanes including butylmethoxydibenzoylmethane (Parsol 1789), salicylates including, homoinenthyl salicylatc, octyl salicylate, trolamine methyl salicylatc; metal oxides including titanium dioxide, zinc oxide and iron oxide; 2-phenylbenziinidazole-5-sulfonic acid; 4,4-methoxy-t-butyldibenzoylmethane; and mixtures thereof.

Further non-limiting examples of sunscreens useful in accordance with the present invention are described in U.S. Pat. No. 5,087,445 to Haffey et al., U.S. Pat. No. 5,073,372 to Turner et al. and U.S. Pat. No. 5,160,731 to Sabatelli et al., all of which are incorporated herein by reference in their entirety.

(b) Anti-wrinkle and Anti-aging Actives

The oil body emulsions of the present invention also may be advantageously formulated with anti-wrinkle and anti-aging actives. These agents include without limitation hydroxy acids including $C_2$–$C_{30}$ alpha-hydroxy acids such as glycolic acid, lactic acid, 2-hydroxy butinoic acid, malic acid, citric acid tartaric acid, alpha-hydroxyethanoic acid, hydroxycaprylic acid and the like; beta hydroxy acids including salicylic acid and polyhydroxy acids including gluconolactone (G4); and mixtures of these acids. Further anti-wrinkle agents include retinoic acid, gamma-linolenic acid; fruit acids, sugar cane extract and glycomer in cross-linked alpha ntutrium; and mixtures thereof. Skin peel agents for example phenol, phytic acid and acetic acid may also be used in accordance with the present invention. Salicylic acid, lactic acid and glycolic acid are preferred for use herein.

(c) Whitening and Bleaching Actives

Whitening and bleaching agents include hydroquinone and derivatives; kojic acid; lactic acid; ascorbyl acid and derivatives such as magnesium ascorbyl phosphate; arbutin; and licorice root. Hydroquinone and derivatives are preferred for use herein.

(d) Sunless Tanning Actives

Sunless tanning actives include dihydroxyacetone (DHA); glyceryl aldehyde; tyrosine and tyrosine derivatives such as malyltyrosine, tyrosine glucosinate, and ethyl tyrosine; phospho-DOPA, indoles and derivatives; and mixtures thereof.

(e) Antimicrobial Actives

Antimicrobials that may be used in accordance with the present invention include all antibiotics, antimicrobial agents and antimicrobial peptides. Antibiotics that may be used include inter alia dermatologically acceptable salts of tetracylin and tetracycline derivatives, gentamycin, kanamycin, streptomycin, neomycin, capreomycin, lineomycin, paromomycin, tobramycin, erythromycin, triclosan, octopirox, paracliirometa xylenol nystatin, tolnafiate, miconazole hydrochloride, chlorhexidine gluconate, chlorhexidin hydrochloride, methanaamine hippurate, methanamine m,andelate, miniocycline hydrochloride, clindamycin, cloecin, b-lactam derivatives such as aminopenicillin and mixtures thereof. Preferred for use herein are chlorhexidin gluconate and tricolosan.

Anti microbial agents that may be used in accordance with the present invention include for example benzoyl peroxide and salicylic acid.

Antimicrobial peptides useful herein are for example magainin, nicin and cecropin.

(f) Anti-acne Actives

Anti-actives that may be used in accordance with the present invention include without limitation keratolytic agents including lactic acid, pyruvic acid, salicylic acids, urea and N-acetylcysteine; retinoids, and retinoid analogs such as tretinoin, cis and trans retinoic acid, retinol and retinol palmitate, isotretinoin-13-cis-retinoic acid; antibiotics and antimicrobial agents such as tetracycline, erythromycin, minocycline, clindamycin, trimethoprim-sulphamethazole and anti-microbial peptides (nicin, for example); steroids, such as hydrocortisone; gainma-linolelnic acid and mixtures tlhereof. Further anti-acne actives that may be used include without limitation benzoyl peroxide; alpha and beta hydroxy acids; sulfacteamide and sulfur and mixtures thereof. Preferably used herein are salicylic acid, benzoyl peroxide and retinoids.

(g) Anti-psoriasis Actives

Anti-psoriasis actives preferred for use in the present invention include without limitation salicylic acid; mometasone furoate; steroids including corticosteroids such as cortisone and oluxclobetasol propionate; 5-fluorouracil; epinephrine; anthralin; vitamin D3 analogs, such as calcipotriene; methotrexate; mnasprocol; trime(thaxate gluconate; retinoids; cyclosporin; paclitaxel; 5-amino levulinic acid; bergasol; tin-ethyl etio puipurin; benzoporphyrin derivatives; antibodies, such as ABX-11.8 antibody, CflDa monoclonal antibody and ICM3 monoclonal antibody; enzyme inhibitors, including tryptase inhibitor and hospholipase A-2 inhibitors; angiogenesis blocking agents; T-cell blocking agents and mixtures thereof.

(h) Anti Eczema Actives

Anti-eczema actives useful herein include urea; evening primrose oil; plant extracts; hydrocortisone; an immunomodulator; tar combined with fatty acids obtained from banana; and mixtures thereofl (i) Topical Anesthetic Actives Topical anesthetic actives that may be used in accordance with the present invention include tetracaine, lidocaine, editocainc, bupivacaine, pramoxine; and mixtures thereof.

(j) Antiinflammatory Actives

Antiinflammatory actives useful in accordance with the present invention include steroidal actives such as hydrocortisone as well as non-steroidal actives including propionic derivatives; acetic acid derivatives; biphenylcarboxylic acid derivatives; fenamic acid derivatives; and oxicams. Examples of antiinflammatorty actives include without limitation acetominaphen, oxaproxin, pranoprofen, benoxaprofen, bucloxic acid, elocon; and mixtures thereof.

(k) Vitamin Actives

Vitamin actives which may be used in accordance with the present invention include vitamin A and derivatives, including retinoic acid, retinyl aldehyde, retin A, retinyl palmitate, adapalene, and beta-carotene; vitamin B (panthelnol, provitamin B5, panthenic acid, vitamin B complex factor); vitamin C (ascorbic acid and salts thereof) and derivatives such as ascorbyl palmitate; vitamin D including calcipotriene (a vitamin D3 analog) vitamin E including its individual constituents alpha-, beta-, gamma-, delta-tocopherol and cotrienols and mixtures thereof and vitamin E derivatives including vitamin E palmitate, vitamin F linolate and vitamin E acetate; vitamin K and derivatives; vitamin Q (ubiquinone) and mixtures thereof.

(1 Protein Actives

One particularly preferred class of actives which may be used in accordance with the present invention are proteins and peptides. Proteins may be formulated in the emulsions of the present invention in any desired manner, however one particularly advantageous way in which proteins may be included in emulsions of the subject invention, is through construction of oleosin gene fusions as detailed in PCT Patent Applicatlon 96/21029 and U.S. Pat. No. 5,650,554 to Moloney both of which are incorporated by reference herein. Briefly stated, PCT Patent Application 96/21029 and U.S. Pat. No. 5,650,554 disclose a method of producing proteins and peptides as fusion proteins of oleosins. These fusion proteins are created by genetically linking the gene encoding oleosin to a gene encoding a peptide or protein of interest. Expression of the fusion gene, in for example an oilseed plant, results in synthesis of a fusion protein which is then targeted to the oil body.

In principle any desired protein or peptide may be produced using this technology and oil bodies comprising these recombinant proteins may be incorporated in the emulsions of the present invention. Proteins and peptides which may be used in accordance with the present invention include enzymes such as proteases (e.g. bromelain, papain, collagenase, elastase), lipases (e.g. phospholipase C), esterases, glucosidases, exfoliating enzymes; antibodies and antibody derived actives, such monoclonal antibodies, polyclonal antibodies, single chain antibodies and the like; reductases; oxidases; peptide hormones; natural structural skin proteins, such as elastin, collagen, reticulin and the like; growth factors such as platelet derived growth factor (PDGF) and epidermis derived growth factor (FOP); antioxidants such as superoxide disinutase, catalase and glutatbione; free-radical scavenging proteins; DNA-repair enzymes, for example T4 endonuclease 5 and P53; antimicrobial peptides, such as magainin and cecropin; a milk protein; a silk protein or peptide; and any active fragments, derivatives of these proteins and peptides; and mixtures thereof.

(m) Miscellaneous Active Ingredients

Further active ingredients that may be formulated in accordance with the present invention include an amino acid and amino acid derivative; an insect repellant; a fungicide (such as ketoconazole); an anti-viral agent (such as acyclovir); an anti-cancer agent; a plant extract; an anti-hemorrhoid compound; an anti-dandruff compound; a hair-growth stimulating compound; a hair loss stimulating compound; a nucleic acid (DNA, RNA and derivatives); an anti-scabies agent (such as permethrin); an anti-wart agent (such as podophyllotoxin); and mixtures thereof.

Miscellaneous Ingredients

A variety of additional ingredients may be formulated into the emulsion formulations of the present invention. These ingredients have been categorized for convenience reasons however this classification is not intended to be limiting to those particular classes or ingredients within those classes (a) Chelating Agents Chelating agents, capable of binding metal ions, such as tartaric acid, EDTA, citric acid, alkali metal citrates, pyrophosphate salts or anionic polymeric polycarboxylates may be also included in the emulsion formulation as desired.

(b) Pigments

Pigments may be also be included in the formulation of the present invention. The pigments that may be used may be white or coloured, inorganic or organic and/or paerlescent. These pigments comprise titanium dioxide, zinc oxide, zirconium dioxide, black, yellow, red and brown iron oxides, cerium dioxide, chromium oxide, ferric blue, carbon black, barium, strontium, calcium and aluminum lakes and mica coated with titanium oxide or with bismuth oxide.

c) Lipids

Lipids that may be used herein include, inter alia, triacyl glycerides; fatty acids such as gamma-linolenic acid; waxes; cholesterol; sphingolipids; ceramides; phospholipids and mixtures thereof.

(d) Inorganic Salts

Inorganic salts that may be used herein include without limitation aluminum zirconium chloride; aluminum chlorohydroxide; zinc oxide; talc; borax; alum; ammonium acetate. These salts are particularly useful in preparing antiperspirants and deodorants.

(e) Anti-oxidants

Anti-oxidants that may be incorporated herein include natural anti-oxidants prepared from plant extracts including without limitation extracts that may be obtained from aloe vera; cryocytol; avocado; chamomile; echinacea; ginko biloba; ginseng; green tea; heather; jojoba; lavender; lemon grass; licorice; mallow; oats; peppermint; St. John's wort; willow; wintergreen; wheat wild yam extract; marine extracts; and mixtures thereof. Further anti-oxidants that may be used include vitamins, including vitamin C, vitamin F. and vitamin E mimetics; alpha-lipoic acid; coenzyme Q; glutathione; superoxide dismutase; and mixtures thereof.

USES OF THE EMULSION FORMULATION

The subject invention is directed toward the production of emulsions that are useful in topical application to the surface area of the human body, including skin, hair, teeth, nails and lips and includes personal care and dermatological products. For the purpose of the present application personal care products are meant to include all cosmetics, cosineceuticals and beauty care products, all of which may be prepared in accordance with the present invention. Dermatological products, for the purpose of the present invention, are meant to include all products to treat or ameliorate skin conditions, abnormalities or diseases and contain one or more active ingredients capable of improving said condition, abnormality, disease. These products include any and all products that may be used to treat or ameliorate any phyiopathological conditions of the dermis or epidermis. Depending on the active ingredient which is formulated, the dermatological products of the present invention may be made available as a prescription drug or as an over-the-counter (OTC) product. It is noted that the emulsions may be applied in compositions which vary considerably in physical properties and use. The types and quantities of ingredients used to prepare different products will depend on the desired use of the product and may be varied in accordance with practices well known to those of ordinary skill in the art of formulating skin care and dermatological products.

Personal Care Products

Personal care products which may be formulated in accordance with the present invention vary widely and include, inter alia, a skin care product, a hair care product, a beauty treatment product, a perfume, a bath and body product, a suncare product, a make-up and a toothpaste. These products may be prepared as formulations intended for specific use by individuals belonging to different age categories (babies, teenagers etc.), having different skin types (e.g. maturing, aged, dry, oily, mixed, combined or complexities thereof or in accordance with the intended functionality of the product (for example products that prevent or reverse dehydration, replenish moisture, modulate pigmentation, prevent or reverse stretch marks, products for treatment or reversal of skin changes associated with aging such as wrinkles, blotches and atrophy or elastotic changes associated with intrinsic aging of the skin, as well as changes caused by external factors for example sunlight radiation, X-ray radiation, air pollution, wind, cold, dampness, dryness, heat, smoke and cigarette smoking)

Examples of skin care products which may be prepared using the emulsion formulations of the present invention include without limitation a skin cream; a facial cream; a cleanser, a toner; a day cream; a night cream; a day lotion; an eye cream; a facial mask (e.g. firming, moisturizing, purifying, deep-cleansing); an anti-aging cream; an anti-wrinkle cream; an anti-puffiness product; a cold weather cream; a foot cream; a facial scrub; an anti-acne product; a hand cream; an insect repellant formulation; or combinations thereof.

Hair care products that may be prepared in accordance with the present invention include for example a shampoo; a conditioner; a re-conditioner; a mousse; a gel; a hair spray; a hair mascara; a hot oil treatment product; a dye; a hair mask; a deep conditioning treatment product; a coloring product; a hair-repair product and permanent wave product or combinations of thereof.

Beauty treatment products include which may be prepared in accordance with the present invention include without limitation, a waxing product, a pedicure product, a manicure product, a facial product, a beauty lift product, a massage product and a aroma-therapy product; and combinations thereof.

Perfumes that may be prepared in accordance with the present invention include without limitation an eau de toilette; an eau de perfume; a perfumed bath, body lotion, shower gel, aftershave etc.; and combinations thereof.

Bath and body products which may be prepared in accordance with the present invention include for example a shower gel; including an exfoliating shower gel; a foaming bath product (e.g. gel, soap or lotion); a milk bath; a body wash; a soap including liquid and bar soap; a cleanser, including a gel cleanser, a liquid cleanser and a cleansing bar; a body lotion; a body spray, mist or gel; an essential lotion; a slimming lotion; bath effervescent tablets; a band and nail cream; a bath/shower gel; a shower cream; a cellulite smoothing product; a deodorant; a dusting powder; an antiperspirant; a depilatory cream; a shaving product e.g. a shaving cream, a gel, a foams and an after-shave, after-shave moisturizer; and combinations thereof.

Suncare products which may be prepared in accordance with the present invention include a sunscreen; a sunblocker; an after sun lotion milks and gel; a burn lotion; a tanning lotion, spray and milk; a sunless self-tanning cream, spray and lotion; a combined sunscreen-insect repellant formulation and combinations thereof.

Make-up products that may be prepared in accordance with the present invention include a mascara (thickening, lengthening, waterproof); a blush (cream and powder); a lipstick; a foundation cream (stick or liquid); a foundation powder, a concealer; an eye shadow (cream and powder); an eye pencil; an eye liquid line; a bronzing powder; a lip pencil; a lip gloss; a lip conditioner; a make-up remover (e.g. eye make-up remover); a liquid lip color; a brow pencil; a lip balm; a nail polish (base and top coat and nail blush); and a combination thereof.

Dermatological Products

The dermatological compositions of the present invention include products which may be used to treat or reverse skin changes associated with aging such as wrinkles, blotches and atrophy or elastotic changes associated with intrinsic aging of the skin as well as changes caused by external factors for example sunlight radiation; X-ray radiation; air pollution; wind; cold; dampness; dryness; heat; smoke and cigarette smoking; external infectious agents such as fungi and bacteria; and combinations thereof.

Additional skin conditions which may be treated include products to treat infectious and non-infectious skin diseases. Infectious diseases include for example impetigo and leprosy. Non-infectious skin diseases include without limitation autoimmune disorders such as psoriasis, cutaneous systemic lupus, cutaneous rheumatoid arthritis, allergic skin disorders (e.g. eczema), and pemphigoid.

Various manifestations of eczema, psoriasis and acne may also be treated using the emulsions of the present invention. Clinical manifestations of eczema which may be treated include, inter alia, atopic eczema; allergic contact dermatitis;

irritant contact dermatitis; infantile seborrhoeic eczema; adult seborrhoeic eczema; varicose eczema and discoid eczema. The manifestations of psoriasis that may be treated include chronic, plaque-type psoriasis; guttato psoriasis; psoriatic erythoderma; and pustular psoriasis. Acne conditions which may be treated include superficial acne (acne vulgaris), low grade acne, pre-acne and acne lesions including comedones and micro coinedones.

Still further examples of dermatological products which may be formulated in accordance with the present invention include without limitation products to treat hyper and hypopigmented skin, age spots, palmar or plantar hyperkeratosis, pruritis ichthyosis, Darier's disease, lichen simplex chronicus, hemorrhoids, inflammatory dermatosis, xeroderma pigmentostim, skin cancers including basal cell carcinoma, malignant cell carcinoma, squamous cell carcinoma, malignant melanoma, and AIDS-related Karposi sarcoma, premalignant skin lesions including actinic keratosis, xerosis, athletes fool, scabies, warts, herpes and dermatoses.

The particular product and the particular form in which the emulsion is applied, however is not of citical importance and may be as desired. It is to be clearly understood that the emulsion formulated with the washed oil body preparation may be applied in any product which is applied to the surface area of the human body.

The following non-limiting examples are illustrative of the present invention. The examples are given solely for the purpose of illustrating the invention and are not to be construed as limitations to the present invention. Variations to these examples are possible without departing from the spirit and the scope of the invention.

EXAMPLES

Example 1

Obtaining a Washed Oil Body Preparation from Oilseed Rape, Soybean, Sunflower, White Mustard, Peanut, Squash, Flax, Safflower and Maize— Laboratory Scale.

Dry mature seeds obtained from Brassica napus cv Westar, soybean, sunflower, white mustard, peanut, squash, flax, safflower and maize were homogenized in five volumes of cold grinding buffer (50 mM Tris-HCl, pH 7.5, 0.4 M sucrose and 0.5 M NaCl) using a polytron operating at high speed. The homogenate was centrifuged at 10×g for 30 minutes in order to remove particulate matter and to separate oil bodies from the aqueous phase containing the bulk of the soluble seed protein. The oil body fraction was skimmed from the surface of the supernatant with a metal spatula and added to one volume of grinding buffer. In order to achieve efficient washing in subsequent steps it was found to be necessary to thoroughly redisperse the oil bodies in the grinding buffer. This was accomplished by gently homogenizing the oil bodies in grinding buffer using a polytron at low speed. Using a syringe, the redispersed oil bodies were carefully layered underneath five volumes of cold 50 mM Tris-HCI pH 7.5 and centrifuged as above. Following centrifugation, the oil bodies were removed and the washing procedure was repeated two times. The final washed oil body preparation was resuspended in one volume of cold Tris-HCI pH 7.5, redispersed with the polytron.

The oil body samples were dissolved in SDS sample buffer and then analyzed by SDS gel electrophoresis. The results are shown in FIG. 1.

The material thus obtained was then ready to be employed in various formulations.

Example 2

Obtaining a Washed Oil Body Preparation from Oilseed Rape, Sunflower and Maize on a Large Scale.

This example describes the recovery of the oil body fraction from canola, sunflower and maize seed on a large scale. The resulting preparation contains intact oil bodies and is comparable in purity with a preparation obtained using laboratory scale procedures.

Grinding of seeds. A total of 10–15 kgs of dry canola seed (Brassica napus cv Westar), sunflower (lielianthus annuus) or maize (Zea mays) was poured through the hopper of a colloid mill (Colloid Mill, MZ-130 (Fryma); capacity: 500 kg/hr), which was equipped with a MZ-120 crosswise toothed rotor/stator grinding set and top loading hopper. Approximately 50–75 litres of water was supplied through an externally connected hose prior to milling. Operation of the mill was at a gap setting of 1 R, chosen to achieve a particle size less than 100 micron at 18° C. and 30° C. Following grinding of the seeds tap water was added to the seed slurry to a final volume of 90 litres.

Removal of solids. The resulting slurry, was pumped into a decantation centrifuge (Hasco 200 2-phase decantation centrifuge maximum operating speed 6,000 rpm) after bringing the centrifuge up to an operating speed of 3,500 rpm. Transfer from the mill to the decantation centrifuge at a flow rate of 360 L/hr was achieved using a 1 inch M2 Wilden air operated double diaphragm pump. In 15–20 minutes approximately 15 kg of seed was decanted.

Oil body separation. Separation of the oil body fraction was achieved using a Sharples Tubular Bowl Centrifuge model AS-16 (Alpha Laval) equipped with a three phase separating bowl and removable ring dam series; capacity:150 L/hr; ringdam: 30 mm. Operating speed was at 15,000 rpm (13,200×g). A Watson-Marlow (Model 704) peristaltic pump was used to pump the decanted liquid phase (DL) into the tubular bowl centrifuge after bringing the centrifuge up to operating speed. This results in separation of the decanted liquid phase into a heavy phase (HP) comprising water and soluble seed proteins and a light phase (LP) comprising oil bodies. The oil body fraction which was obtained after one pass through the centrifuge is referred to as an unwashed oil body preparation. The oil body fraction was then passed through the centrifuge three more times. Between each pass through the centrifuge, concentrated oil bodies were mixed with approximately five volumes of fresh water. The entire procedure was carried out at room temperature. The preparations obtained following the second separation are all referred to as the washed oil body preparation. Following three washes much of the contaminating Soluble. protein was removed and the oil body protein profiles obtained upon SDS gel electrophoresis were similar in appearance to those obtained using laboratory scale procedures.

The large scale oil body preparation may be pasteurized. Pasteurization is achieved by initially thickening the washed oil bodies with centrifugation to a water content of 30 to 60%, preferable between 35 and 50% weight and most preferable between 37 and 40% weight. The thickened oil body solution can then be pasteurized in a constant temperature water bath at approximately 65° C. for 20 minutes. The pasteurization temperature could range between 50 and 90° C. and the time for pasteurization could range between 15 seconds to 35 minutes. If the oil bodies are used in a cosmetic formulation, then before pasteurization, 0.1% Glydant Plus, 0.1% BHA and 0.1% BHT may be added as a preservative and anti-oxidants respectively.

Example 3

Removal of Seed Proteins by Washing the Oil Body Phase.

This example describes the recovery of a washed oil body fraction from canola, maize and sunflower seed. Using different washing conditions, it is shown that the washes result in the removal of significant amounts of seed proteins from the oil body preparation. These proteins include proteins which might be allergenic.

A total of 10–15 kgs of dry canola seed (*Brassica napus* cv Westar), maize (*Zea mays*) or sunflower (*Helianithus annuus*) was poured through the hopper of a colloid mill (Colloid Mill, MZ-130 (Fryma)), which was equipped with a MZ-120 crosswise toothed rotor/stator grinding set and top loading hopper. Approximately 50–75 l water was supplied through an externally connected hose prior to milling. Operation of the mill was at a gap setting of 1R, chosen to achieve a particle size less than 100 micron at 18° C. and 30° C. Following grinding of the seeds, tap water was added to the seed slurry to a final volume of 60–90 litres and a sample of the seed slurry was obtained for SDS gel electrophoresis. The slurry was then pumped into a decantation centrifuge (Hasco 200 2-phase decantation centrifuge maximum operating speed 6,000 rpm) after bringing the centrifuge up to an operating speed of 3,500 rpm. Transfer from the null to the decantation centrifuge was achieved using a 1 inch M2 Wilden air operated double diaphragm pump. In 15–20 minutes approximately 15 kg of seed was decanted. A sample from the decanted liquid phase was obtained for SDS gel electrophoresis. Separation of the oil body fraction was achieved using a Sharples Tubular Bowl Centrifuge model AS-16 (Alpha Laval) equipped with a three phase separating bowl and removable ring dam series; capacity: 150 L/hr; ringdam: 29 mm. Operating speed was at 15, 000 rpm (13,2000×g). A Watson-Marlowe (Model 704) peristaltic pump was used to pump the decanted liquid phase into the tubular bowl centrifuge after bringing the centrifuge up to operating speed. The unwashed oil body phase was obtained and mixed with approximately 5 volumes of water. This procedure was repeated a total of three more times. The oil body phase which was obtained following the first spin, is referred to as an unwashed oil body preparation. All other preparations are washed oil body preparations. Samples for analysis by SDS gel electrophoresis were obtained following the first and fourth separations.

Upon completion of the fourth wash a 0.9 ml sample of the oil body preparation was homogenized in 0.1 ml 1 M $Na_2CO_3$ and left at room temperature for 30' with agitation. The washed oil body fraction was then recovered following centrifugation, washed once with water and prepared for SDS gel electrophoresis.

Figure 2:
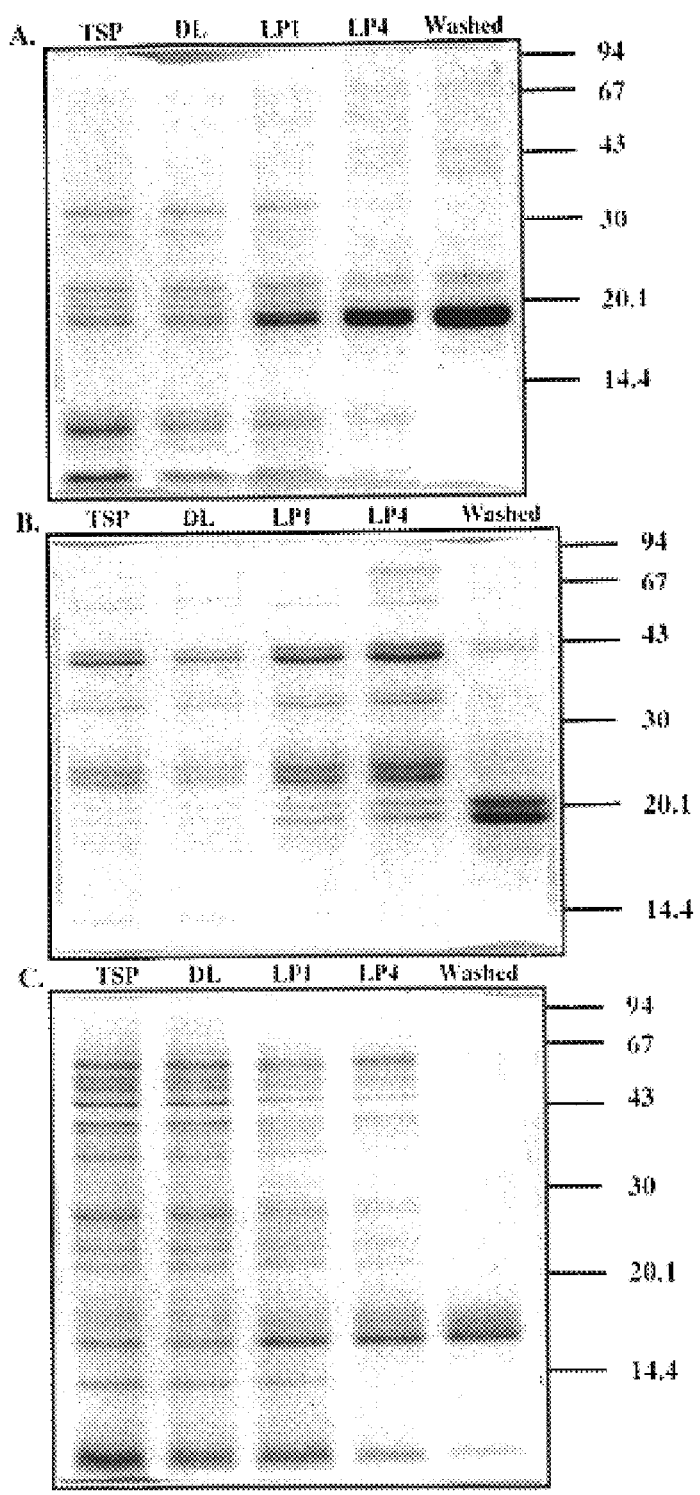
FIGS. 2A–C are Coomassie blue stained gels showing the protein profiles of various seed fractions obtained from *Brassica napus* (Canola) (A), sunflower (B), and maize (C). The gels show the following fractions (1) total seed protein (TSP), (2) decanted liquid phase (DL), (3) unwashed oil bodies (LP1), (4) three washes with water (LP4), (5) four washes with water and one wash with 100 mM $Na_2CO_3$ (Washed).

All of the samples were dissolved in SDS sample buffer and the samples were analyzed by SDS gel electrophoresis. The results are shown in FIG. 2.

Example 4
The Effect of Washing the Oil Body Phase on Water Retention Characteristics.

A washed oil body preparation and an unwashed oil body phase were prepared from rapeseed as in example 2. To determine the difference in water retention capacity between the unwashed oil body phase and the washed oil body preparation, 30 mls of oil body preparations were thoroughly mixed using a vortex. The preparations were then incubated for 2 hours in a water bath at 40, 60 or 80° C. and the samples were centrifuged at 1,500×g for 20 minutes (undiluted samples). Another set of samples was prepared by mixing 15 g of washed or unwashed oil body preparation with 15 ml of water. The samples were mixed on a vortex and then incubated at 40, 60 or 80° C. for 2 hours and the amount of water present in the samples was determined following centrifugation at 1,500×g for 20 minutes (diluted samples). Loss of mass attributable to evaporation was measured at 80 ° C. and 60° C.

At 80° C., the undiluted preparations comprising oil bodies lost significant amounts of water through evaporation. The preparation of unwashed oil bodies lost 26% of their mass, while the washed preparation lost 16%. Upon centrifugation the unwashed preparation released approximately 2.5 ml of aqueous phase, while the washed oil bodies remained in the same phase. Both diluted preparations absorbed water. The volume of oil bodies increased in both cases to 18.5±1 ml.

At 60° C., the undiluted preparations lost approximately 10% of water through evaporation. Following centrifugation, the washed preparation released about 0.5 ml of aqueous phase, while the washed oil body preparation stayed in the same phase. Both diluted preparations absorbed water. At 60° C., the volume of oil bodies increased in both cases to 18±1 ml.

At 40° C., the undiluted samples both released approximately 2 ml of aqueous phase. When the diluted samples weire compared, the unwashed preparation absorbed about 3 ml of water, as was the case at 60 or 80° C. However the washed preparation absorbed 8 ml of water at 40° C.

These experiments demonstrate that in a washed oil body preparation heated to 60° C. or 80° C., water remains more tightly associated with the oil body preparation than in an unwashed preparation. When cooled down the washed oil body preparation appeared to be more stable than the unwashed emulsion. When heated to 40° C., the washed oil body preparation was able to absorb a larger volume of exogenously added water without resulting in phase separation offering greater flexibility in preparing oil body based formulations.

Example 5
The Effect of Washing Oil Bodies on Oil Absorption Characteristics.

A washed oil body preparation and an unwashed oil body phase were prepared from rapeseed as in example 2. To determine the difference in oil absorption capacity between the unwashed oil body phase and the washed oil body preparation, 2 grams of the oil body preparations was dispersed into 12 ml of refined, bleached, deodorized canola oil in a 50 ml tube. The contents were stirred for 30 seconds every 5 minutes for 30 min. The tubes were then centrifuged at 4,400 rpm for 25 min. The free oil was decanted and the percentage of absorbed oil was determined by weight difference. Three preparations of washed oil bodies were tested and three preparations of unwashed oil bodies were tested.

The oil absorption capacity of unwashed oil bodies was found to vary significantly between the three batches and varied from 18.7% to 28%. Washed oil bodies had reproducible oil absorption of 32±1%. Thus the washed oil body preparation was found to be superior since (1) a larger amount of oil was found to be absorbed and (2) the absorption occurred in a more reproducible manner.

Example 6
Preparation of Stabilized Oil Body Emulsions Comprising Washed Safflower Oil Bodies for Use of Formulation in a Personal Care Product (Base Formulations A, B, C).

A washed oil body preparation was prepared from safflower seeds as described in example 2. The oil bodies were transferred into a mixing pot and 0.7% keltrol was added. The mixture was then vigorously stirred at room temperature. Subsequently 2.0% glycerin was added. The mixture was then heated to 45–50° C. and 0.1% butylated hydroxyanisole (BHA) and 0.1% butylated hydroxytoluene (BHT) were added. Finally 0.15% Glydant Plus was added. The procedure for Base B and C was slightly different as the temperature was subsequently increased to 60° C. and 2.5% Arlacel 165 was added and mixed until a preparation of homogeneous appearance was obtained. The mixture was then rapidly cooled to 30° C. under moderate stirring.

| Base A | |
|---|---|
| Hydrated safflower oil bodies (0.1% Glydant Plus, 0.1% BHT, 0.1% BHA) | 96.95% |
| Glydant Plus | 0.15% |
| BHT | 0.1% |
| BHA | 0.1% |
| Keltrol | 0.7% |
| Glycerine | 2.0% |
| Base B | |
| Hydrated safflower oil bodies (0.1% Glydant Plus, 0.1% BHT, 0.1% BHA) | 95.45% |
| Glydant Plus | 0.15% |
| BHT | 0.1% |
| BHA | 0.1% |
| Keltrol | 0.7% |
| Glycerine | 2.0% |
| Arlacel | 2.5% |
| Base C | |
| Hydrated safflower oil bodies (0.1% Glydant Plus, 0.1% BHT, 0.1% BHA) | 94.75% |
| Glydant Plus | 0.25% |
| BHT | 0.1% |
| BHA | 0.1% |
| Keltrol | 0.3% |
| Glycerine | 2.0% |
| Arlacel | 2.5% |

The formulations thus prepared were found to be stable with respect to color, odor, viscosity, oxidation, pH and microbial levels for a period of at least 3 months at 45° C. The stability at 45° C. can be extraolated into a stability of approximately 2 years at room temperature. The chemical analysis of the hydrated safflower oil body preparation revealed that the sample contained 50.82% water and 49.18% dry weight. The dry weight (DW) component consisted of 3.76% protein, 93.56% oil and 2.68% other.

Example 7

Preparation of a Cosmetically Elegant Product from Base B.

Base B was used to formulate a cosmetically elegant product as follows. The water soluble ingredients keltrol, panthenol and allantoin were dissolved using moderate agitation at room temperature. Once these ingredients were dissolved, glycerin was added while mixing was continued. The water phase was then heated to a final temperature of 75° C. to 77° C. The oil phase was prepared in a separate mixing pot with moderate agitation and subsequently heated to 75° C. to 77° C. The oil phase soluble ingredients that were used were Dimethicone 350, Cetyl Alcohol, Arlacel 165, Finsolv TN, Sesame Oil, Vitamin E Acetate, and Phenonip. The oil phase and water phase were mixed under vigorous agitation for 15 minutes. The resulting emulsion was then gradually cooled to 40° C. and agitation was gradually diminished. At approximately 40° C., Base Formulation B was slowly added to the emulsion. The mixture was then allowed to cool to room temperature.

| Keltrol | 0.5% |
|---|---|
| Panthenol | 0.1% |
| Allantoin | 0.05% |
| Glycerin | 2.0% |
| Dimethicone | 1.0% |
| Arlacel 165 | 2.5% |
| Cetyl Alcohol | 2.0% |
| Finsolv TN | 2.0% |
| Sesame Oil | 1.0% |
| Vitamin E Acetate | 0.05% |
| Phenonip | 1.0% |
| Base Formulation B | 10.0% |
| Water | 77.8% |

Example 8

Preparation of a Cosmetically Elegant Product from Base C.

Base C was further formulated and a cosmetically elegant product for topical application was prepared as follows. The water phase soluble ingredients keltrol, panthenol and allantoin were dissolved using moderate agitation at room temperature. When all ingredients were dissolved glycerin was added while mixing was continued. The water phase was then heated to a final temperature of 75° C. to 77° C. The oil phase was prepared in a separate mixing pot using moderate agitation and heated up to 75° C. to 77° C. The oil phase ingredients that were used were Dimethicone 350, Cetyl Alcohol, Arlacel 165, Finsolv TN, Isohexadecane, Vitamin E Acetate, and Phenonip. The two phases were mixed using vigorous agitation with for 15 minutes. The mixture was then gradually cooled to 40° C. The agitation was gradually decreased as the temperature decreased. At approximately 40° C. Base Formulation C was added slowly to the emulsion. The final formulation was then allowed to cool to room temperature.

| Keltrol | 0.5% |
|---|---|
| Panthenol | 0.1% |
| Allantoin | 0.05% |
| Glycerin | 2.0% |
| Dimethicone | 1.0% |
| Arlacel 165 | 2.5% |
| Cetyl Alcohol | 2.0% |
| Finsolv TN | 2.0% |
| Isohexadecane | 2.0% |
| Vitamin E Acetate | 0.05% |
| Phenonip | 1.0% |
| Base Formulation C | 20.0% |
| Water | 66.8% |

Example 9

Preparation of a Cosmetically Elegant Product from Base B.

Base B was further was used for formulation in a cosmetically elegant formulation for topical application using the following procedure. The water soluble ingredients keltrol, panthenol and allantoin were dissolved at room temperature under moderate stirring conditions. Glycerin was then added with continued mixing and the water phase was heated to a final temperature of 75° C. to 77° C. The oil phase was prepared in a separate mixing pot with moderate agitation and then subsequently heated up to 75° C. to 77° C. The oil phase ingredients included, SEE 839, Cetyl Alcohol, Arlacel 165, Finsolv TN, Vitamin F Acetate, and Phenonip. The oil phase was then added to the water phase and mixed under vigorous agitation conditions for 15 minutes. The mixture was then gradually cooled to 40° C. At approximately 40° C. Base Formulation B was slowly added to the emulsion. The final formulation was allowed to cool off to room temperature.

| Keltrol | 0.5% |
|---|---|
| Panthenol | 0.1% |
| Allantoin | 0.05% |
| Glycerin | 2.0% |
| SEE 839 | 1.0% |
| Arlacel 165 | 2.5% |
| Cetyl Alcohol | 2.0% |
| Finsolv TN | 2.0% |
| Vitamin E Acetate | 0.05% |
| Phenonip | 1.0% |
| Base Formulation B | 40.0% |
| Water | 48.8% |

Example 10
Preparation of a Sunscreen with a Sun Protection Factor of 8.

Bases B was used to prepare a cosmetically elegant sunscreen. The water soluble ingredients keltrol, panthenol and allantoin were dissolved under moderate agitation at room temperature. The glycerin was then added with continued mixing. The water phase was heated to a final temperature of 75° C. to 77° C. The oil phase was prepared in a separate mixing pot under moderate agitation and heated to 75° C. to 77° C. The oil phase ingredients included: Dimethicone, Cetyl Alcohol, Arlacel 165, Finsolv TN, Sesame Oil, Vitamin E Acetate, Parsol MCX and Phenonip. Emulsification involved mixing of the oil phase and the water phase. The two phases were mixed under vigorous agitation conditions for 15 minutes. The mixture was then gradually cooled to 40° C. At approximately 40° C. Base Formulation B was added slowly. The mixture is allowed to cool to room temperature.

| Keltrol | 0.5% |
|---|---|
| Panthenol | 0.1% |
| Allantoin | 0.05% |
| Glycerin | 2.0% |
| Dimethicone | 1.0% |
| Arlacel 165 | 2.5% |
| Cetyl Alcohol | 2.0% |
| Finsolv TN | 2.0% |
| Sesame Oil | 1.0% |
| Vitamin E Acetate | 0.05% |
| Phenonip | 1.0% |
| Base Formulation B | 10.0% |
| Water | 70.3% |
| Parsol MCX | 7.5% |

Example 11
Preparation of a Sunscreen.

The water soluble ingredients Kaolin and Veegum Ultra were dissolved under moderate agitation at room temperature. The glycerin was then added. The water phase was heated to a final temperature of 75° C. to 77° C. and methylparaben is added. The oil phase was prepared in a separate mixing pot using moderate agitation and heated to 75° C. to 77° C. The oil phase ingredients that were used were Dimethicone 250, Cetyl Alcohol, Arlacel 165, Propylparaben, Safflower Oil, Trivalin SF, Palemol OL and Parsol MCX. The oil an water phases were subsequently mixed under vigorous agitation for 15 minutes. The mixture was then gradually cooled to 40°C, while gradually decreasing agitation. At 40° C., Germall 115 was added and when the temperature reached about 37° C. to 40° C. the safflower oil body preparation was added slowly. The mixture was allowed to cool to room temperature and the colorant (red 33 solution) was added. The final pH was 6.0 and viscosity was 25,000 cps.

| Purified Water | 47.15% |
|---|---|
| Kaolin USP | 2.50% |
| Veegum Ultra (Mg, Al Sillicate) | 5.00% |
| Glycerin | 2.00% |
| Methylparaben | 0.30% |
| Dimethicone 350 | 0.50% |
| Cetyl Alcohol | 2.00% |
| Arlacel 165 (Glyceryl Stearate & PEG-100 Stearate) | 2.50% |
| Propylparaben | 0.15% |
| Safflower Oil | 2.00% |
| Trivalin SF (Ethyoxydiglycol) | 2.00% |
| Palemol OL (Oleyl Lactate) | 1.00% |
| Parsol MCX (Octyl Methoxycinnamate) | 7.50% |
| Germall 115 (Imidazolidinyl Urea) | 0.30% |
| Hydrated Safflower Oil Body (0.1% Glydant Plus, 0.1% BHT, 0.1% BHA) | 25.00% |
| Red #33 1% | 0.10% |

Example 12
Preparation of a Skin Care Cream Containing a Stable Vitamin A Derivative, Retinyl Palmitate.

The water soluble ingredient Keltrol, Panthenol and Allantoin were dissolved under moderate agitation at room temperature. The glycerin was then added while mixing was continued. The water phase was heated to a temperature of 75° C. to 77° C. The oil phase was prepared in a separate mixing pot under moderate agitation and subsequently heated to 75° C. to 77° C. The oil phase ingredients used were Dimethicone 350, Cetyl Alcohol, Arlacel 165, Finsolv TN, Permethyl 101A, Phenonip and Retinyl Palmitate. The two phases were mixed under vigorous agitation for 15 minutes. The mixture was then gradually cooled to 40° C. The agitation was decreased as the temperature decreased. At 40° C. the Base Formulation C was slowly added.

| Keltrol | 0.5% |
|---|---|
| Panthenol | 0.1% |
| Allantoin | 0.05% |
| Glycerin | 2.0% |
| Dimethicone | 1.0% |
| Arlacel 165 | 2.5% |
| Cetyl Alcohol | 2.0% |
| Finosolv TN | 2.0% |
| Permethyl 101 A | 2.0% |
| Phenonip | 1.0% |
| Base Formulation C | 50.0% |
| Water | 35.85% |
| Retinyl Palmitate | 1.0% |

Example 13
Preparation of a Day Cream.

The water soluble ingredients kaolin and the Mg, Al Silicate were dissolved at room temperature. The glycerin is then added while mixing continued. The water phase was heated to a final temperature of 75° C. to 77° C. The oil phase was prepared in a separate mixing pot using moderate agitation and then subsequently heated up to 75° C. to 77° C. The oil phase ingredients that were used were Dimethicone 350, Cetyl Alcohol, Arlacel 165, Trivalin SP, and Palemol OL. The two phases were then mixed using vigorous agitation for 15 minutes. The mixture was then cooled gradually to 40° C. At 40° C. Germaben 11 was added and when the temperature reached about 37° C. to 40° C. the safflower oil bodies were slowly added. The mixture was then allowed to cool to room temperature. The final pH was adjusted to 6.00 with a final viscosity of 25,060 cps.

| Purified water | 32.20% |
|---|---|
| Kaolin | 2.50% |
| Veegum Ultra (Mg, Al Silicate) | 5.00% |
| Glycerin | 2.00% |
| Dimethicone 350 | 0.50% |
| Cetyl Alcohol | 2.00% |
| Arlacel 165 (Glyceryl Stearate & PEG-100 Stearate) | 2.50% |
| Trivalin SF (Ethoxydiglycol) | 2.00% |
| Palemol OL (Oleyl Lactate) | 1.00% |
| Germaben II (Diazolidinyl Urea) | 0.30% |
| Hydrated Safflower Oil Body (0.1% Glydant Plus, 0.1% BHT, 0.1% BHA) | 50.00% |

Example 14
Preparation of a Night Cream.

The water soluble ingredients Kaolin, Mg and Al Silicate were dissolved using moderate agitation at room temperature. Glycerin was added while mixing continued. The water phase was heated to a temperature of 75° C. to 77° C. The oil phase was prepared in a separate mixing pot using moderate agitation and heated up to 75° C. to 77° C. The oil phase ingredients used were Dimethicone 350, Cetyl Alcohol, Arlacel 165, Trivalin Sr, and Palemol OL. The two phases were mixed under vigorous agitation for 15 minutes. The mixture was then cooled gradually to 60° C. The agitation was gradually decreased as the temperature decreased. At 60° C. glycolic acid was added, at 50° C. a 25% solution of sodium hydroxide was added, at 40° C. the Germall 115 was added and when the temperature reached about 37 to 40° C. the safflower oil bodies were added slowly. The final pH was adjusted to 3.64 with a final viscosity of 35,000 cps.

| Purified water | 24.20% |
|---|---|
| Kaolin | 2.50% |
| Veegum Ultra (Mg, Al Silicate) | 5.00% |
| Glycerin | 2.00% |
| Dimethicone 350 | 0.50% |
| Cetyl Alcohol | 2.00% |
| Arlacel 165 (Glyceryl Stearate & PEG-100 Stearate) | 2.50% |
| Trivalin SF (Ethoxydiglycol) | 2.00% |
| Palemol OL (Oleyl Lactate) | 1.00% |
| Glycolic Acid | 8.00% |
| Sodium Hydroxide (25% solution) | qs pH 3.3–3.8 |
| Germaben H (Diazolidinyl Urea) | 0.30% |
| Hydrated Safflower Oil Body (0.1% Glydant Plus, 0.1% BHT, 0.1% BHA) | 50.00% |

Example 15
Preparation of a Facial Mask.

The water soluble ingredients kaolin, Mg, Al Silicate were dissolved using moderate agitation at room temperature. Glycerin was then added under continued mixing. The water phase was heated to a temperature of 75° C. to 77° C. and methylparaben, Green Clay and Bentonite NP BC were added. The oil phase was prepared in a separate mixing pot under moderate agitation and then subsequently heated up to 75° C. to 77° C. The oil phase ingredients used were Dimethicone 350, Trivent OC-G, Arlacel 165, Polyparabin and Safflower Oil. The two phases were mixed under vigorous agitation for 15 minutes. The mixture was then cooled slowly to 40° C. At 40° C. Germall 115 and phytic acid were added. When the temperature reached about 37° C. to 40° C. the safflower oil bodies were added slowly.

| Distilled Water | 44.25% |
|---|---|
| Kaolin | 2.50% |
| Glycerin | 2.00% |
| Methylparaben | 0.30% |
| Green Clay (Montmorillonate) | 2.00% |
| Bentonite NF BC | 10.00% |
| Dimethicone 350 | 0.50% |
| Trivent OC-G (Tricaprylin) | 2.00% |
| Glyceryl Stearate & PEG-100 Stearate | 2.00% |
| Propylparabin | 0.15% |
| Safflower oil | 1.00% |
| Ethoxydiglycol | 3.00% |
| Germall 115 (Imidazolidinyl Urea) | 0.30% |
| Hydrated Safflower oil body (0.1% Glydant Plus, 0.1% BHT, 0.1% BHA) | 25.00% |
| Phytic Acid | 5.0% |

Example 16
Comparison of Washed Oil Bodies and Lipid Vesicles in the Preparation of Cosmetic Formulations.

Washed Oil bodies were prepared as described in example 2, pasteurized and 0.1% BHT, 0.1% BHA and 0.31%/ Glydant plus added. Lipid vesicles were prepared in accordance with the specification of U.S. No. Pat. 5,683,740 except that they were prepared from safflower seed, pasteurized and 0.1%, BST, 0.1% BHA and 0.1% Glydant Plus was added.

The oil bodies and lipid vesicles were compared with respect to emulsion stability, color changes, odor changes, viscosity, microbial growth and cosmetic desirability parameters. To evaluate stability, the samples were tested at 45° C., 4° C. and room temperature (3 months at 45° C. is equivalent to approximately 2 year shelf life at room temperature). To evaluate emulsion stability, 150 g of each sample was maintained at 45° C., 75 g of each sample was maintained at room temperature or at 4° C. Emulsion stability was evaluated for emulsion separation, oil droplet separation and coalescence. The 4° C. sample was used as the reference for comparison. Color changes were evaluated by visual inspection. Color was evaluated on the accelerated oven sample (45° C.) and the room temperature sample and compared to the 4° C. as a reference. Odor was tested as with the color with the 4° C. sample used as a reference point. In order to maintain consistency, the odor was judged by two individuals who both agreed on the evaluation. Viscosity of each sample was measured at room temperature using a RVT Model viscometer with Spindle E at 10 prm. Microbial growth was measured on 10 g (if each sample, The sample was diluted and 1 ml of the sample is added to 49° C. Tryptic Soy Agar, swirled and allowed to cool. The plates were incubated at 35° C. for 48 hours and a colony count was taken. Finally, cosmetic attributes were evaluated by 3 individuals, 2 individuals who were familiar with oil bodies/ lipid vesicles and 1 person who was not. Cosmetic attributes include skin penetration, residue left on the skin after the sample was rubbed in, dryness (lack of moisture) and oiliness.

Table 1 summarizes the results for the oil bodies. The pH for the oil body sample was constant at 6.50 throughout the test at room temperature and at 45° C. The oil body preparation, when applied to the skin, distributed evenly on the skin, was fast penetrating and left almost no residue on the skin surface. The oil body preparation was also stable with respect to color, odor, viscosity and emulsion stability.

Table 2 summarizes the results for the lipid vesicles. The pH for the lipid vesicle sample is difficult to measure because of the total separation but was approximately 6.8. The lipid vesicle preparation, when applied to the skin, was very oily and left a film residue on the skin. The lipid vesicle preparation was stable with respect to microbial growth but was not stable with respect to color, odor and emulsion stability.

The above results demonstrate that the oil washed oil body preparation is clearly superior to lipid vesicles with respect to both physical parameters (color, odor, stability) and cosmetic parameters (penetration, residual residue, and oiliness). These parameters are critical to the preparation of personal care products.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

We claim:

1. A topical emulsion formulation comprising washed oil bodies and an active agent wherein the actine agent is an antibody.

2. An emulsion formulation according to claim 1 wherein said active agent is cross-linked to the oil body.

3. An emulsion according to claim 1 wherein the oil bodies are obtained from a plant.

4. An emulsion according to claim 3 wherein the oil bodies are obtained from a plant selected from the group consisting of rapeseed (Brassica spp.), soybean (*Glycine max*), sunflower (*Helianthus unnuus*), oil palm (*Elaeis guineeis*), cottonseed (Gossypium spp.), groundnut (*Arachis hypogaea*), coconut (*Cocus nucifera*), castor (*Ricinus communis*), safflower (*Carthamus tinctorius*), mustard (Brassica spp. and *Sinapis alba*), coriander, (*Coriandrum sativum*), squash (*Cucurbita maxima*), linseed/flax (*Linum usitatissimum*), Brazil nut (*Bertholletia excelsa*) jojoba (*Simmondsia chinensis*) and maize (*Zea mays*).

5. An emulsion according to claim 1 wherein said washed oil bodies are substantially intact.

6. A personal care product comprising an emulsion according to claim 1.

7. A personal care product according to claim 6 wherein said personal care product is selected from the group consisting of skin care product, a hair care product, a beauty treatment product, bath and body product, a suncare product, and a toothpaste.

8. A dermatological product comprising an emulsion according to claim 1.

TABLE 1

| Time (days) | Color | Odor | Stability | Viscosity (cps) | Microbial Growth |
|---|---|---|---|---|---|
| Room Temperature | | | | | |
| 0 | Pale yellow | Very Mild | No separation | 3500 ± 100 | 500 |
| 14 | Pale yellow | No change | No separation | 3500 ± 100 | 300 |
| 25 | Pale yellow | No change | No separation | 3500 ± 100 | <10 |
| 45° C. | | | | | |
| 0 | Pale yellow | Very Mild | No separation | 3500 ± 100 | 500 |
| 14 | Pale yellow | Mild | No separation | 4000 ± 100 | <20 |
| 25 | Mildly yellow | Mild | No separation | 4000 ± 100 | <10 |
| 4° C. | | | | | |
| 0 | Pale yellow | Very Mild | No separation | 3500 ± 100 | 500 |
| 14 | Pale yellow | Very Mild | No separation | 3500 ± 100 | 250 |
| 25 | Pale yellow | Very Mild | No separation | 3500 ± 100 | <10 |

TABLE 2

| Time (days) | Color | Odor | Stability | Viscosity (cps) | Microbial Growth |
|---|---|---|---|---|---|
| Room Temperature | | | | | |
| 0 | Dark yellow | Very Mild | Separation | Approx. 4000 | <20 |
| 14 | Dark yellow | Very Mild | Total Separation | Sluggish | <20 |
| 25 | Darker yellow | Very Mild | Total Separation | Sluggish | <10 |
| 45° C. | | | | | |
| 0 | Dark yellow | Neutral | No separation | 3500 ± 100 | <20 |
| 14 | Brown | Amine Odor | No separation | 4000 ± 100 | <10 |
| 25 | Dark brown | Fishy | No separation | 4000 ± 100 | <10 |
| 4° C. | | | | | |
| 0 | Dark yellow | Neutral | Separation | Approx. 4000 | <20 |
| 14 | Dark yellow | Neutral | No separation | 3500 ± 100 | <10 |
| 25 | Dark yellow | Neutral | No separation | 3500 ± 100 | <10 |

9. A dermatological product comprising an emulsion according to claim 8 wherein said dermatological product is used to treat psoriasis, eczema, hemorrhoids, lupus, leprosy, acne, athlete's foot, xerosis, scabies, warts, herpes and dermatoses.

10. A personal care product according to claim 7 wherein said bath and body product is a body wash.

* * * * *

UNITED STATES PATENT AND TRADEMARK OFFICE
CERTIFICATE OF CORRECTION

PATENT NO. : 6,372,234 B1
DATED : April 16, 2002
INVENTOR(S) : Deckers et al.

It is certified that error appears in the above-identified patent and that said Letters Patent is hereby corrected as shown below:

Column 4,
Line 44, change "Trn" to -- During --;

Column 5,
Line 8, change "w1w" to -- w/w --;

Column 10,
Line 40, change "plh" to -- pH --;

Column 14,
Line 5, change "cationic,s" to -- cationics --;

Column 19,
Line 24, change "avidil" to -- avidin --;
Line 44, change "IJVC" to -- UVC --;

Column 22,
Line 18, change "disinutase" to -- dismutase --;
Lines 18 and 19, change "glutabione" to -- glutatione --;

Column 23,
Line 19, change "cosineceuticals" to -- cosmeceuticals --;

Column 25,
Line 18, change "fool" to -- foot --;

Column 27,
Line 19, change "null" to -- mill --;

Column 29,
Line 41, change "extraolated" to -- extrapolated --;

Column 35,
Line 11, change "oil washed oil" to -- water washed oil --;

UNITED STATES PATENT AND TRADEMARK OFFICE
CERTIFICATE OF CORRECTION

PATENT NO.   : 6,372,234 B1
DATED        : April 16, 2002
INVENTOR(S)  : Deckers et al.

It is certified that error appears in the above-identified patent and that said Letters Patent is hereby corrected as shown below:

<u>Column 36,</u>
Line 3, change "actine" to -- active --

Signed and Sealed this

Twenty-sixth Day of November, 2002

Attest:

Attesting Officer

JAMES E. ROGAN
*Director of the United States Patent and Trademark Office*